(12) United States Patent
Ferree

(10) Patent No.: US 7,291,171 B2
(45) Date of Patent: Nov. 6, 2007

(54) ARTIFICIAL DISC REPLACEMENT (ADR) USING ELASTIC TETHER MEMBER

(76) Inventor: Bret A. Ferree, 1238 Cliff Laine Dr., Cincinnati, OH (US) 45208

( * ) Notice: Subject to any disclaimer, the term of this patent is extended or adjusted under 35 U.S.C. 154(b) by 249 days.

(21) Appl. No.: 10/680,468

(22) Filed: Oct. 7, 2003

(65) Prior Publication Data

US 2004/0111155 A1    Jun. 10, 2004

Related U.S. Application Data

(63) Continuation-in-part of application No. 10/434,931, filed on May 9, 2003, and a continuation-in-part of application No. 10/434,917, filed on May 9, 2003, and a continuation-in-part of application No. 10/435,332, filed on May 9, 2003, now Pat. No. 6,875,235.

(60) Provisional application No. 60/445,958, filed on Feb. 7, 2003, provisional application No. 60/445,489, filed on Feb. 6, 2003, provisional application No. 60/443,815, filed on Jan. 30, 2003, provisional application No. 60/422,971, filed on Jan. 27, 2003, provisional application No. 60/417,346, filed on Oct. 9, 2002, provisional application No. 60/416,749, filed on Oct. 7, 2002, provisional application No. 60/379,462, filed on May 10, 2002.

(51) Int. Cl.
*A61F 2/44* (2006.01)
(52) U.S. Cl. .................. 623/17.11; 623/17.13
(58) Field of Classification Search ... 623/17.11–17.16
See application file for complete search history.

(56) References Cited

U.S. PATENT DOCUMENTS

| | | | | |
|---|---|---|---|---|
| 4,309,777 A | 1/1982 | Patil | ............ | 623/17.13 |
| 4,759,769 A | 7/1988 | Hedman et al. | ............ | 623/17.13 |
| 5,002,576 A | 3/1991 | Fuhrmann et al. | ............ | 623/17.15 |
| 5,389,107 A | 2/1995 | Nassar et al. | ............ | 623/23 |
| 5,458,642 A | 10/1995 | Beer et al. | ............ | 623/17.13 |
| 5,676,702 A | 10/1997 | Ratron | ............ | 623/17.16 |
| 5,865,846 A | 2/1999 | Bryan et al. | ............ | 128/898 |
| 5,989,291 A | 11/1999 | Ralph et al. | ............ | 623/17.15 |
| 6,001,130 A | 12/1999 | Bryan et al. | ............ | 623/17.16 |
| 6,022,376 A | 2/2000 | Assell et al. | ............ | 623/17.16 |
| 6,063,121 A | 5/2000 | Xavier et al. | ............ | 623/17.15 |
| 6,136,031 A | 10/2000 | Middleton | ............ | 623/17.16 |
| 6,156,067 A | 12/2000 | Bryan et al. | ............ | 623/17.15 |
| 6,264,695 B1 * | 7/2001 | Stoy | ............ | 623/17.16 |
| 6,296,664 B1 | 10/2001 | Middleton | ............ | 623/17.15 |

(Continued)

FOREIGN PATENT DOCUMENTS

WO     WO 0059412     10/2000

(Continued)

*Primary Examiner*—Suzette Gherbi
(74) *Attorney, Agent, or Firm*—Gifford, Krass, Sprinkle, Anderson & Citkowski, PC

(57) ABSTRACT

Artificial disc (ADR) and joint replacement components, particularly those associated with the knee and hip, use compressible, resilient materials to approximate natural kinematics, often in conjunction with elastic or spring components to tether articulating components to avoid dislocation, excessive compression, flexion or other out-of-range movements. The preferred embodiments require only two or a few articulating components. The designs allow for normal flexion, extension, lateral bending, rotation, and translocation, depending upon the application.

2 Claims, 21 Drawing Sheets

U.S. PATENT DOCUMENTS

| | | | |
|---|---|---|---|
| 6,315,797 B1 | 11/2001 | Middleton | 623/17.16 |
| 6,478,822 B1* | 11/2002 | Leroux et al. | 623/17.14 |
| 6,488,710 B2* | 12/2002 | Besselink | 623/17.15 |
| 6,508,841 B2 | 1/2003 | Martin et al. | 623/23.12 |
| 6,520,996 B1 | 2/2003 | Manasas et al. | 623/23.5 |
| 6,527,806 B2 | 3/2003 | Ralph et al. | 623/17.16 |
| 6,558,424 B2* | 5/2003 | Thalgott | 623/17.16 |
| 6,582,466 B1* | 6/2003 | Gauchet | 623/17.11 |
| 6,645,248 B2* | 11/2003 | Casutt | 623/17.12 |
| 6,656,178 B1* | 12/2003 | Veldhuizen et al. | 606/61 |
| 6,706,067 B2* | 3/2004 | Shimp et al. | 623/17.11 |
| 7,018,416 B2* | 3/2006 | Hanson et al. | 623/17.16 |
| 2003/0199979 A1* | 10/2003 | McGuckin, Jr. | 623/17.11 |
| 2004/0073310 A1* | 4/2004 | Moumene et al. | 623/17.13 |
| 2004/0220672 A1* | 11/2004 | Shadduck | 623/17.16 |
| 2004/0225361 A1* | 11/2004 | Glenn et al. | 623/17.12 |
| 2005/0125063 A1* | 6/2005 | Matge et al. | 623/17.13 |
| 2005/0197702 A1* | 9/2005 | Coppes et al. | 623/17.12 |
| 2006/0247778 A1* | 11/2006 | Ferree et al. | 623/17.14 |
| 2007/0050033 A1* | 3/2007 | Reo et al. | 623/17.12 |

FOREIGN PATENT DOCUMENTS

WO    WO 00/64385    11/2000

* cited by examiner

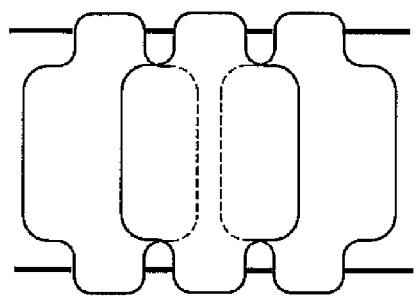
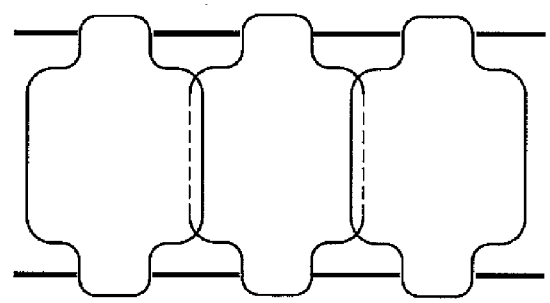
*Fig - 34A*       *Fig - 34B*
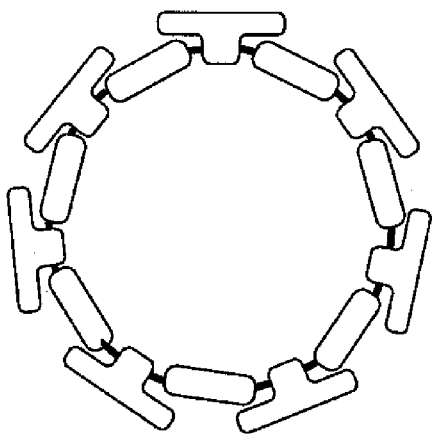
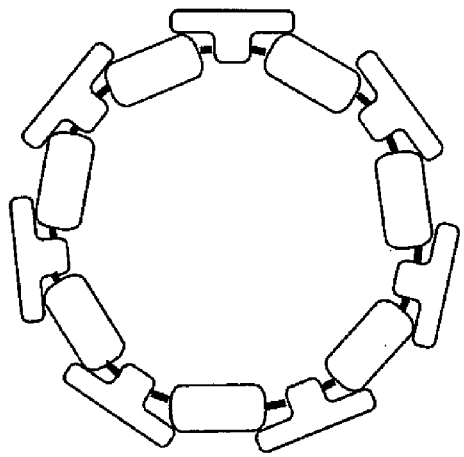
*Fig - 35A*       *Fig - 35B*
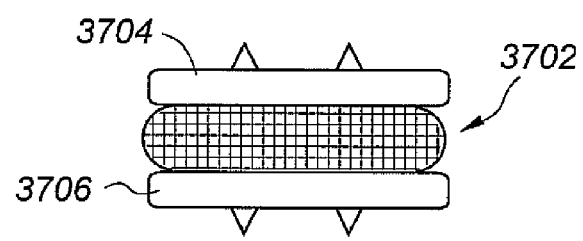
*Fig - 36*       *Fig - 37A*

ARTIFICIAL DISC REPLACEMENT (ADR) USING ELASTIC TETHER MEMBER

REFERENCE TO RELATED APPLICATIONS

This application claims priority from U.S. Provisional Patent Application Ser. Nos. 60/416,749, filed Oct. 7, 2002; 60/417,346, filed Oct. 9, 2002; 60/442,971, filed Jan. 27, 2003; 60/443,815, filed Jan. 30, 2003; 60/445,489, filed Feb. 6, 2003; 60/445,958, filed Feb. 7, 2003. This application is also a continuation-in-part of U.S. patent application Ser. Nos. 10/434,931, filed May 9, 2003; 10/434,917, filed May 9, 2003; and 10/435,332, filed May 9, 2003 now U.S. Pat. No. 6,875,235 which claims priority from 60/379,462, filed May 10, 2002. The content of each application is incorporated herein by reference.

FIELD OF THE INVENTION

This invention relates generally to prosthetic implants and, in particular, to artificial intervertebral disc and joint replacement components with improved wear and kinematics.

BACKGROUND OF THE INVENTION

Improvements in prosthetic intervertebral disc and joint replacement components, and related surgical procedures, have led to dramatic increases in implant longevity. Many artificial hip and knee components now last for twenty years or more due to improved materials and greater insight into movement, load distribution and wear characteristics.

Many spinal conditions, including degenerative disc disease, can now be treated through artificial disc replacement (ADR), which has several advantages over spinal fusion. The most important advantage of ADR is the preservation of spinal motion. Spinal fusion eliminates motion across the fused segments of the spine. Consequently, the discs adjacent to the fused level are subjected to increased stress, which increases the changes of future surgery to treat the degeneration of the discs adjacent to the fusion.

One of the most important features of an artificial disc replacement (ADR) is its ability to replicate the kinematics of a natural disc. ADRs that replicate the kinematics of a normal disc are less likely to transfer additional forces above and below the replaced disc. In addition, ADRs with natural kinematics are less likely to stress the facet joints and the annulus fibrosus (AF) at the level of the disc replacement. Replicating the movements of the natural disc also decreases the risk of separation of the ADR from the vertebrae above and below the ADR.

The kinematics of joint replacements in general and ADRs in particular are governed by range of motion (ROM), the location of the center(s) of rotation (COR), and other such considerations. Clearly any improvements in these and other areas would be welcomed by the medical community and by patients undergoing procedures to implant prosthetic components of this kind.

SUMMARY OF THE INVENTION

This invention is broadly directed to improved artificial disc (ADR) and joint replacement components, particularly those associated with the knee and hip. Most embodiments use compressible, resilient materials to approximate joint kinematics, often with elastic or spring components to tether articulating components to avoid dislocation, excessive compression, flexion or other out-of-range movements. The preferred embodiments include a robust design, requiring only two or a few articulating components. The designs allow for normal flexion, extension, lateral bending, rotation, and translocation, depending upon the application.

Most ADR embodiments do not require precise alignment. The ADR can be self-centering in versions that articulate with the endplates of the vertebrae. Alternative vertebral endplate resurfacing designs are also disclosed. Typical ADR embodiments combine a compressible component and a C-shaped or other containment component, to accommodate natural axial forces, relaxation, and bending movements. Further embodiments use the ADR EPs to force or wedge apart articulating components made of metal, or other material with good wear characteristics, as loads are applied.

In all embodiments, the articulating components may be surrounded and/or connected by a material or materials with elastic properties. The elastic material or materials force the assembled disc or joint replacement to assume its resting size and shape once the loads are removed. Other embodiments utilize components that articulate with a spring component. Further embodiments incorporate one or more springs in conjunction with one or more dampening materials, preferably hydrogels, elastomers, polyurethanes, foam polyurethanes, or other polymers to protect against the full loads of the spine.

In different embodiments, membranes may be used to prevent the ingrowth of tissue, to trap debris or to contain lubricating fluid such as vegetable oil or saline, a gel other than hydrogel, or a viscoelastic fluid. The springs can be made of metals such as titanium, Nitinol, stainless steel or other metals. Polymeric elastomers or other high performance fibers can also provide spring properties. The articulating components and the ADR EPs can be made of ceramic, titanium, chrome cobalt, or other material commonly used in orthopaedic implants. A fully assembled disc or joint replacement may be inserted after compression with a tool, or cemented in the disc space with polymethylacrylate or other cement.

BRIEF DESCRIPTION OF THE DRAWINGS

FIG. 34A is a view of the side of the spring component drawn in FIG. 33A;

FIG. 34B is a view of the side of the spring component drawn in FIG. 34A during compression of the springs;

FIG. 35A is a view of the top of the spring component drawn in FIG. 34A;

FIG. 35B is a view of the top of the compressed spring component drawn in FIG. 34B;

FIG. 36 is a cross section view of the hoops and leaf springs drawn in FIG. 34A;

FIG. 37A is a view of the side of another embodiment of an ADR according to the invention;

FIG. 68 is a sagittal cross section through another ADR embodiment;

FIG. 69A is a sagittal cross section of another embodiment of the ADR;

FIG. 69B is a sagittal cross section of another version of the ADR of FIG. 69A;

FIG. 70A is a sagittal cross section through another TKR embodiment of the invention;

FIG. 70B is a sagittal cross section of another version of the invention of FIG. 70A;

FIG. 70C is a sagittal cross section of another configuration of the device of FIG. 70B; and FIG. 70D is an axial cross section of the embodiment of the TKR of FIG. 70A.

DETAILED DESCRIPTION OF THE INVENTION

Figure 1:
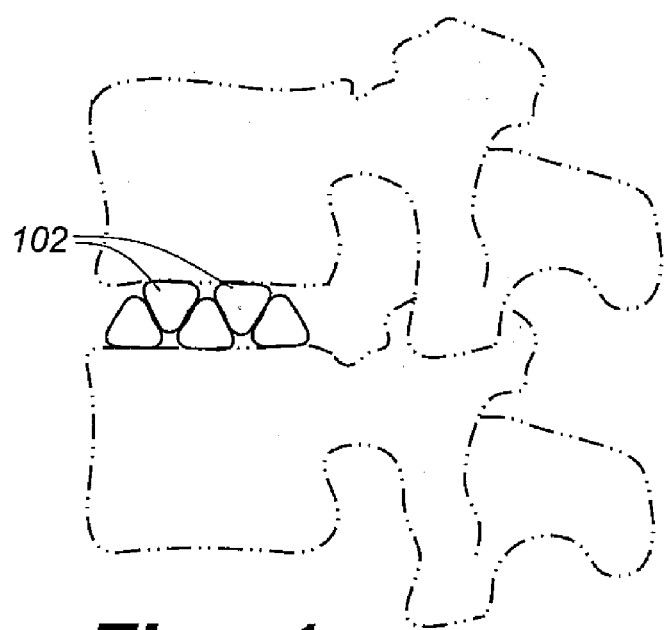
FIG. 1 is a view of the lateral aspect of the spine and an artificial disc replacement (ADR) according to the invention.
Figure 2:
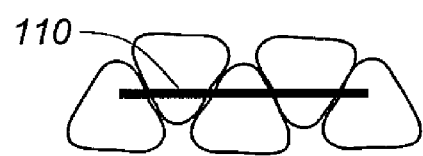
FIG. 2 is a sagittal cross section of the ADR of FIG. 1.

FIG. 1 is a view of the lateral aspect of the spine and an ADR according to the invention, including a plurality of articulating components 102. FIG. 2 is a sagittal cross section of the ADR, illustrating how the articulating components are connected by one or more springs or elastic bands 110. Using this configuration, the articulating components are free to position themselves to "custom fit" the endplates of the vertebrae.

Figure 3:
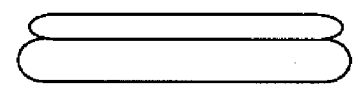
FIG. 3 is a view of the anterior aspect of the ADR of FIG. 1.
Figure 4:
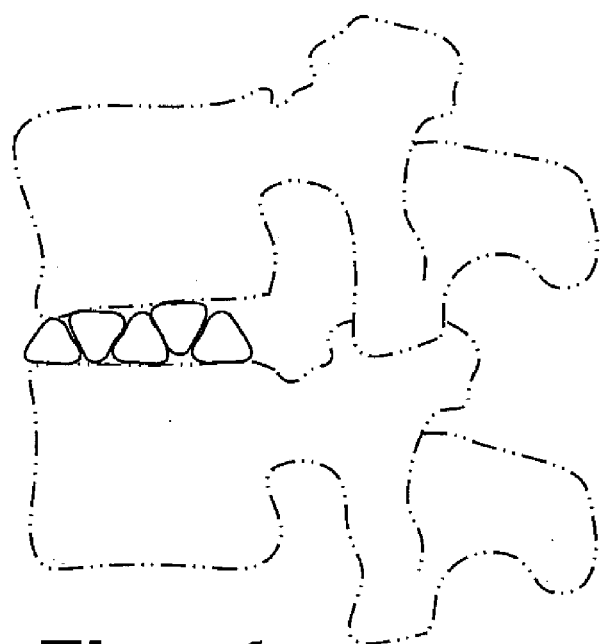
FIG. 4 is a view of the lateral aspect of a flexed spine and the ADR of FIG. 1.

FIG. 3 is a view of the anterior aspect of the ADR, and FIG. 4 is a view of the lateral aspect of the ADR in conjunction with a flexed spine. The anterior components slide against one another to decreases the height of the anterior aspect of the ADR during spinal flexion. The elastic tether returns the articulating components to their resting position as the spine is returned to its neutral position. The articulating components and the elastic tether also cooperate to dampen axial loads to the spine.

Figure 5:
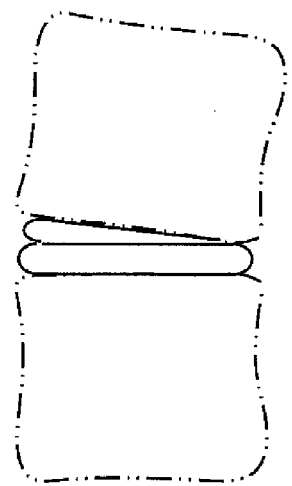
FIG. 5 is a view of the anterior aspect of spine bent to the left and the ADR.

FIG. 5 is a view of the anterior aspect of spine bent to the left and the ADR, showing how the articulating components slide against each other to facilitate lateral bending of the spine.

Figure 6:
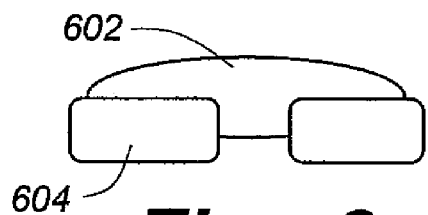
FIG. 6 is a view of the anterior surface of an artificial disc replacement (ADR) according to the invention.
Figure 7:
FIG. 7 is a view of the lateral aspect of the ADR of FIG. 6.
Figure 9:
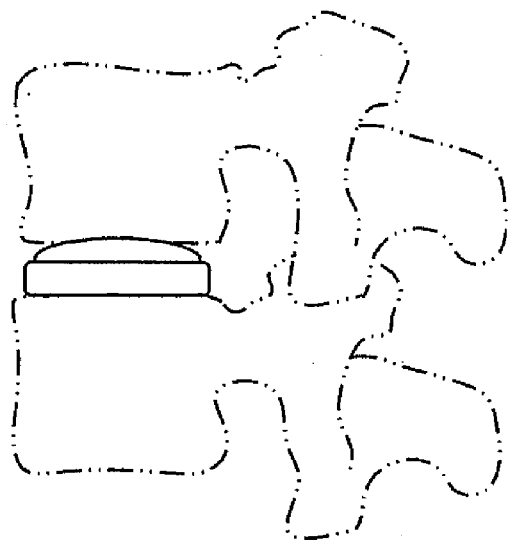
FIG. 9 is a lateral view of the spine and the ADR of FIG. 6.
Figure 8:
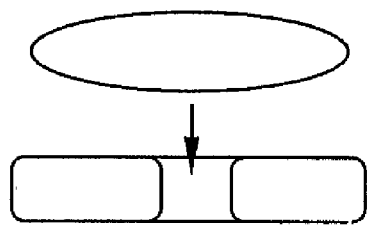
FIG. 8 is an exploded view of the anterior aspect of the ADR of FIG. 6.
Figure 10B:
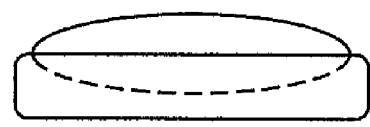
FIG. 10B is a view of the anterior aspect of the ADR of FIG. 6.
Figure 10A:
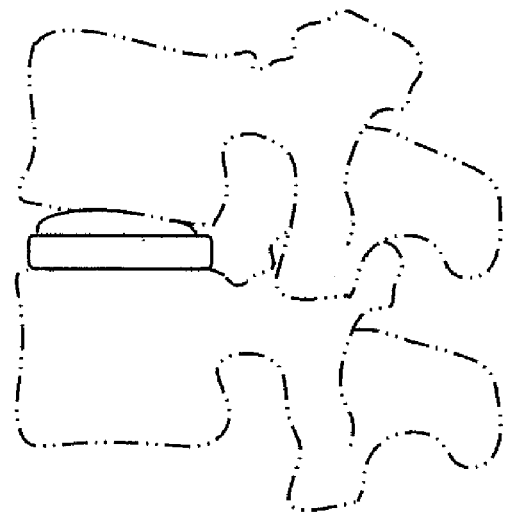
FIG. 10A is a lateral view of the spine and the ADR of FIG. 6.
Figure 10C:
FIG. 10C is view of the anterior aspect of the ADR of FIG. 6.

FIG. 6 is a view of the anterior surface of an ADR according to the invention including a biconvex component 602. A C-shaped inferior component 604 preferably includes a spring-like shape memory. FIG. 7 is a view of the lateral aspect of the ADR of FIG. 6, and FIG. 8 is an exploded view. FIG. 9 is a lateral view of the spine and the ADR of FIG. 6, and FIG. 10A is a lateral view of the spine and the ADR of FIG. 6. FIG. 10B is a view of the anterior aspect of the ADR. The dotted line shows the position of the inferior surface of the biconvex component within the C-ring spring component. FIG. 10C is view of the anterior aspect of the ADR. As in FIG. 10B, the dotted line represents the position of the inferior surface of the biconvex component.

Figure 11B:
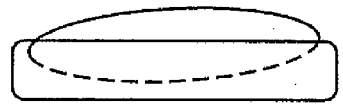
FIG. 11B is a view of the lateral aspect of the ADR of FIG. 6 in a flexed position.
Figure 11C:
FIG. 11C is a view of the anterior aspect of the ADR of FIG. 6 in a flexed position.
Figure 11A:
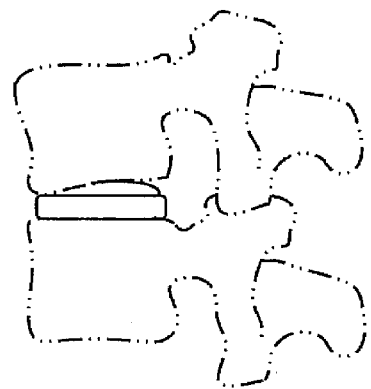
FIG. 11A is a lateral view of a flexed spine and the ADR of FIG. 6.

FIG. 11A is a lateral view of a flexed spine and the ADR. FIG. 11B is a view of the lateral aspect of the ADR in a flexed position, showing how the anterior surface of the biconvex component tilts and is forced into the C-ring spring component. Thus, the height of the anterior aspect of the ADR decreases with flexion of the spine. The C-ring spring returns the biconvex component to its neutral position as pressure is relieved from the anterior aspect of the spine. Similarly, axial loads on the spine are cushioned by the interaction of the biconvex component with the C-ring spring.

FIG. 11C is a view of the anterior aspect of the ADR in a flexed position. The anterior portion biconvex component can be seen to extend closer to the inferior surface of the C-ring spring component in FIG. 11C when FIG. 11C is compared to FIG. 10C. The opening of the C-ring spring is larger in FIG. 11C than the opening of the C-ring spring of the ADR in the neutral position of FIG. 10C.

Figure 12:
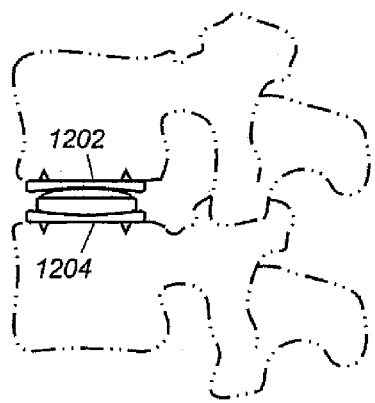
FIG. 12 is a view of the lateral aspect of the spine, an ADR, and optional resurfacing components placed over the endplates of the vertebrae.

FIG. 12 is a view of the lateral aspect of the spine and the ADR showing optional resurfacing components 1202, 1204 over the endplates of the vertebrae. The endplate resurfacing components preferably include bone ingrowth on the vertebral portion of the components. The ADR can also be used with the "mobile link" described in my co-pending U.S. patent application Ser. No. 10/426,995, the entire content of which is incorporated herein by reference.

Figure 13:
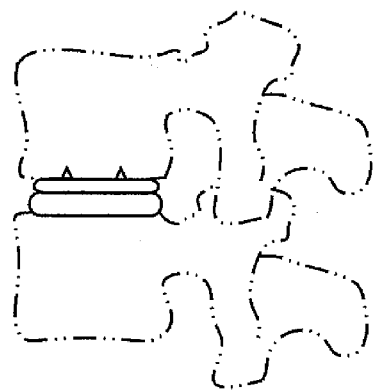
FIG. 13 is a lateral view of the spine and an alternative embodiment of the invention.
Figure 14A:
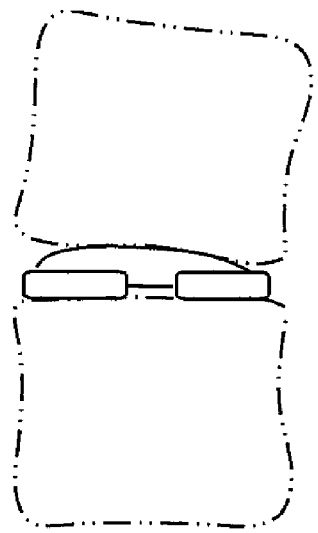
FIG. 14A is a view of the anterior aspect of the spine and the ADR of FIG. 13.
Figure 14B:
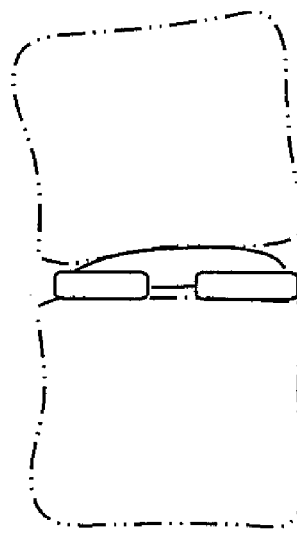
FIG. 14B is a view of the anterior aspect of the spine and the ADR of FIG. 13.

FIG. 13 is a lateral view of the spine and an alternative embodiment of the ADR wherein the superior component includes a bone ingrowth upper surface. FIG. 14A is a view of the anterior aspect of the spine and the ADR with the spine positioned to show side bending to the left. FIG. 14B is a view of the anterior aspect of the spine and the ADR with the spine positioned to show side bending to the right.

Figure 15:
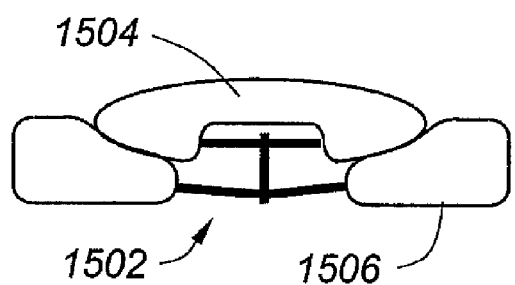
FIG. 15 is coronal cross section of an ADR and optional link members connecting the two components of the ADR.

FIG. 15 is coronal cross section of an ADR according of the invention showing optional link members 1502 connecting the two ADR components 1504, 1506. The portion of the link member across the C-shaped spring component allows the C-shaped to open and close. In this example, a relatively lax cable connects the two side of the C-shaped component.

Figure 16:
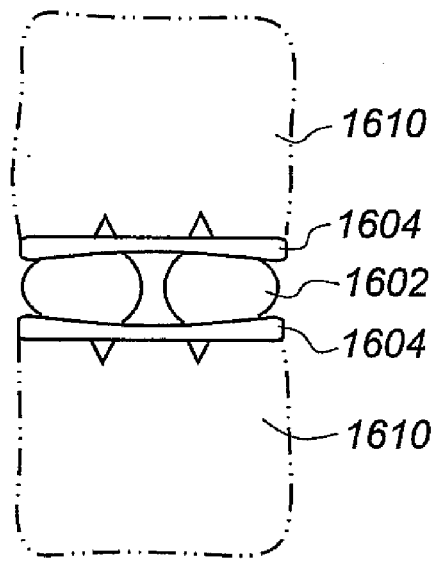
FIG. 16 is a coronal cross section of the spine and an ADR according to the invention.
Figure 17:
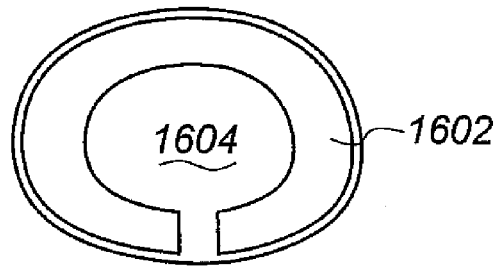
FIG. 17 is an axial cross section of a spring component and an ADR endplate from the ADR of FIG. 16.
Figure 18:
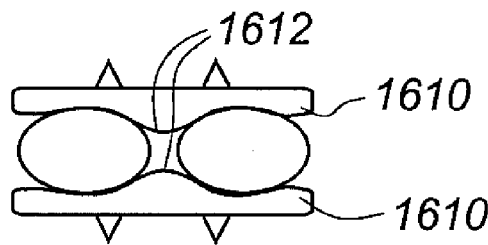
FIG. 18 is a coronal cross section of another version of the ADR of FIG. 16.

FIG. 16 is a coronal cross section of the spine and an ADR including a horizontal, generally C-shaped spring component 102 that articulates with endplates 104 over the surfaces of vertebral bodies 110. FIG. 17 is an axial cross section of the spring component and an ADR endplate 104. FIG. 18 is a coronal cross section of another embodiment of the ADR drawn in FIG. 16, wherein one or both of the endplates 110 may have raised areas 112 to help the spring component open when axial loads are applied to the ADR. The anterior location of the opening of the spring component facilitates spinal flexion.

Figure 19A:
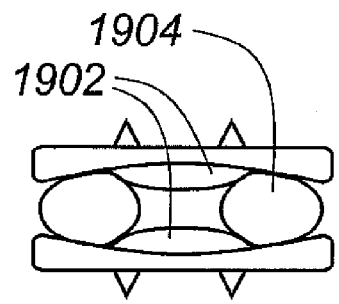
FIG. 19A is a coronal cross section of an alternative embodiment of the invention.
Figure 19B:
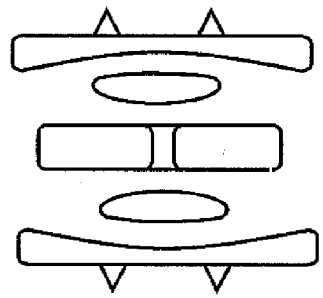
FIG. 19B is an exploded view of the ADR of FIG. 19A.

FIG. 19A is a coronal cross section of an alternative embodiment of the invention including spacer components 1902 that articulate between the ADR endplates and the spring 1904. FIG. 19B is an exploded view of the ADR of FIG. 19A. The spacer components 1902 facilitate opening of the spring, while allowing translation of the ADR endplates relative to the spring with spinal movement.

Figure 20A:
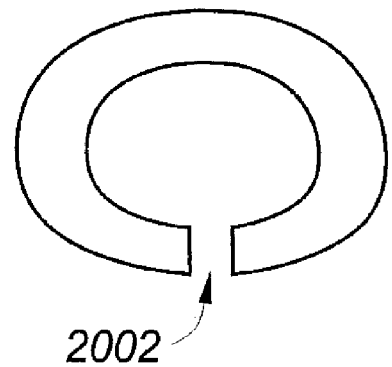
FIG. 20A is a view of the top of a circular or oval spring with an anterior opening.
Figure 20C:
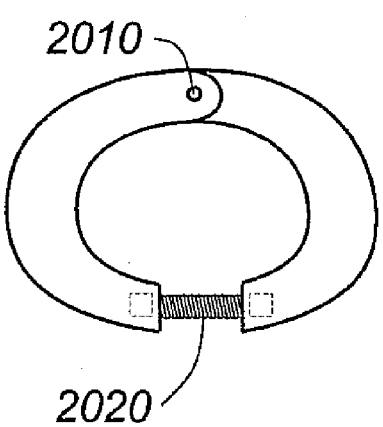
FIG. 20C is a view of the top of an alternative spring component.
Figure 20B:
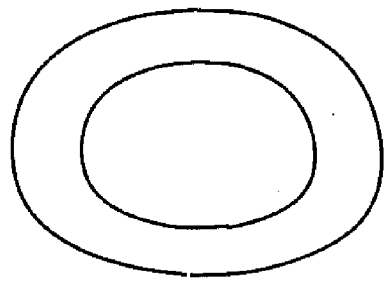
FIG. 20B is a view of the top of an alternative spring component without an opening.

FIG. 20A is a view of the top of a circular or oval-shaped spring component with an anterior opening 2002. The opening of a circular shaped spring is more likely to rotate away from an anterior location. FIG. 20B is a view of the top of an alternative oval-shaped spring component without an opening. FIG. 20C shows an alternative spring component having two or more components joined together through a joint that allows a relative degree of motion. An axle 2010 is used to connect the pieces in the example drawn. An elastic tether or spring 2020 on the anterior portion of the assembled spring component enables the use of metals with hard articulating surfaces, but poor elastic properties.

Figure 21:
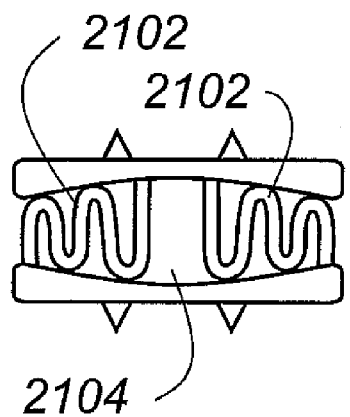
FIG. 21 is a coronal cross section of an ADR including an alternative spring component designed to resist radial forces.

FIG. 21 is a coronal cross section through an embodiment of the ADR with an alternative spring component 2102 designed to resist radial forces. Furthermore, the spring component 2102 is compressible in a superior to inferior direction. The superior to inferior compressibility of the spring allow tilting and translation of the ADR endplates. A compressible, resilient material such as an elastomer or hydrogel is preferably placed with central portion 2104 of the spring in the preferred embodiment of the device. Axial load on the ADR endplates is transferred to radial force on the spring. The preferred spring component in this embodiment of the device, as illustrated in the example drawn in FIG. 20B, does not contain an opening. If a hydrogel is used, the central component imbibes fluid after insertion and the spring with shape memory properties, increases in height after insertion between the ADR endplates.

Figure 22A:
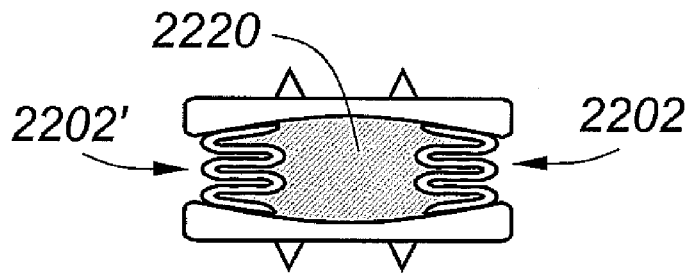
FIG. 22A is a coronal cross section of yet a further alternative embodiment of the invention.
Figure 22B:
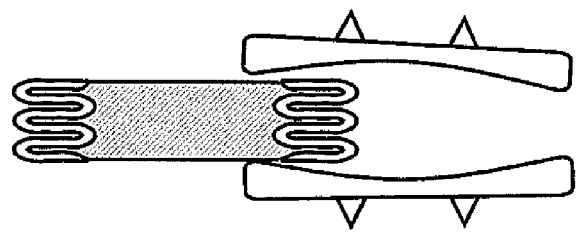
FIG. 22B is a coronal cross section of the ADR drawn in FIG. 22A during the insertion process.

FIG. 22A is a coronal cross section of yet a further alternative embodiment of the invention featuring a differently shaped spring component 2202. Again, the cavity within the spring component 702 is at least partially filled with an elastomer, hydrogel or other compressible, resilient material 2220. FIG. 22B is a coronal cross section of the ADR drawn in FIG. 22A during the insertion process. As discussed in FIG. 21, the spring and central material expands vertically after insertion between the ADR endplates.

Figure 23:
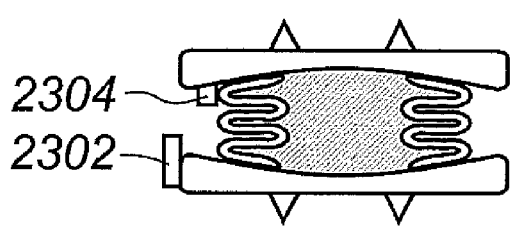
FIG. 23 is a sagittal cross section of an embodiment with components to help prevent extrusion of the modular spring component.

FIG. 23 is a sagittal cross section of an embodiment of the device with components to help prevent extrusion of the modular spring component, including projections 2304 from the superior endplate and attachable pieces 2302 on the inferior endplate. The projections can be spring loaded or rotated (i.e., at 90 degrees) into position.

Figure 24:
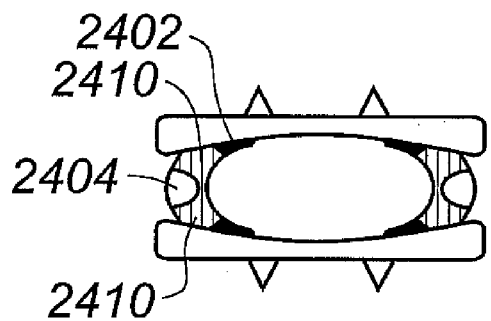
FIG. 24 is a coronal cross section of an embodiment of the invention incorporating a composite spring.

FIG. 24 is a coronal cross section of an embodiment of the invention utilizing a composite spring. Area 2402 of the spring represents the hard less flexible portion of the spring, whereas the area 2404 of the spring represents the more flexible portion. The area of the spring 2410 between areas 2402, 2404 represents an optional area of the composite with intermediate properties. Hydrogel or other elastomer is preferably placed within the composite spring.

Figure 25:
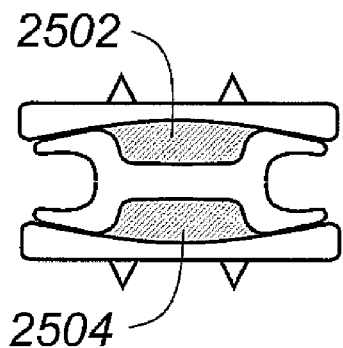
FIG. 25 is a coronal cross section of an embodiment of the invention with an alternative spring component.

FIG. 25 is a coronal cross section of an embodiment of the device with an alternative spring component. Again, the areas 2502, 2504 preferably contain a hydrogel, elastomer, or other compressible, resilient material.

Figure 26:
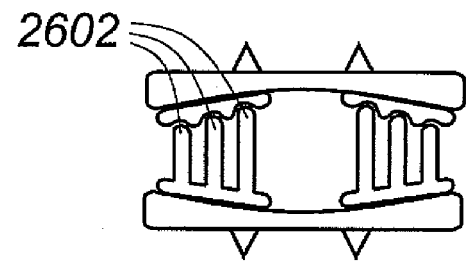
FIG. 26 is a coronal cross section of an embodiment of the invention with a different alternative spring component.

FIG. 26 is a coronal cross section of an embodiment of the device with an alternative spring component featuring closely spaced concentric rings 2602. As in FIGS. 21-25 the spring component is flexible in a superior to inferior direction. The spring also expands slightly in a radial direction.

Figure 27:
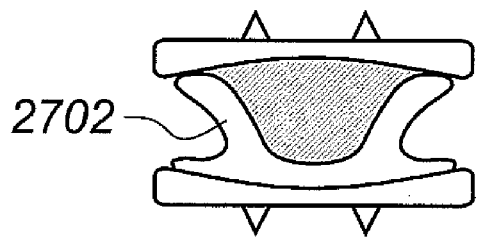
FIG. 27 is a coronal cross-section of yet another embodiment of the invention.
Figure 28:
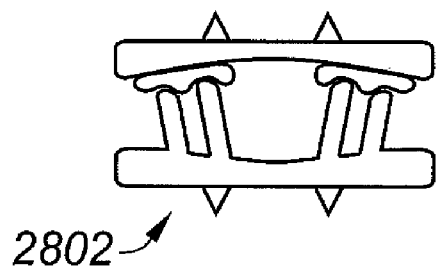
FIG. 28 is a coronal cross section of an alternative embodiment of the invention, wherein the spring component forms part of one of the endplates.
Figure 29:
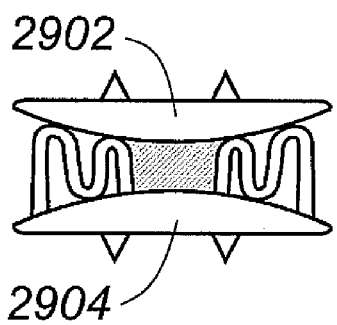
FIG. 29 is a coronal cross section of an alternative embodiment, wherein the endplates are convex.

FIG. 27 is a coronal cross-section of another embodiment of the invention including a spring component 2702. FIG. 28 is a coronal cross section of an alternative embodiment, wherein the spring component 2802 forms part of one of the endplates. Note that the spring components in other embodiments, such as those depicted in of FIGS. 21-26, can also be incorporated into one of the endplates. FIG. 29 is a coronal cross section of an alternative embodiment, wherein the endplates 2902, 2904 are convex. Alternatively, the ADR endplates can be flat, concave or a more complex shape. It is also possible to use ADR endplates with different shapes in a single ADR.

Figure 30:
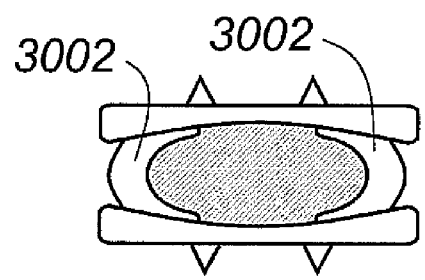
FIG. 30 is a coronal cross-section of yet a further alternative embodiment of the invention incorporating a hoop-like spring.
Figure 31:
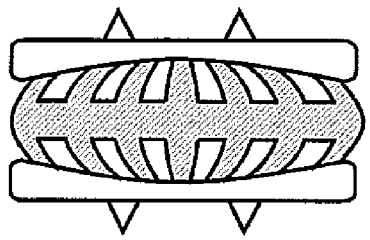
FIG. 31 is a coronal cross section of another embodiment, wherein the spring component has vertical separations through the top and bottom of the spring.
Figure 32:
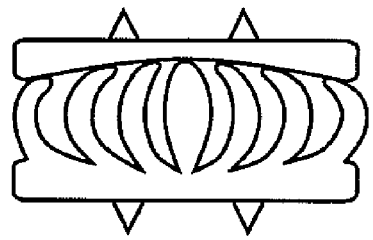
FIG. 32 is a coronal cross-section of another embodiment of the device drawn in FIG. 31, wherein the vertical spring members are an integral part of one of the ADR endplates.

FIG. 30 is a coronal cross section of yet a further alternative embodiment of the invention incorporating a hoop-like spring 3002. FIG. 31 is a coronal cross section of another embodiment, wherein the spring component has vertical separations through the top and bottom of the spring which make it easier for the spring to bend in a superior to inferior direction. Hydrogel-containing embodiments of the device may place a membrane between the hydrogel and the spring to help hold the hydrogel within the spring. FIG. 32 is a coronal cross section of a variation of the device drawn in FIG. 31, wherein the vertical spring members are an integral part of one of the ADR endplates.

Figure 33A:
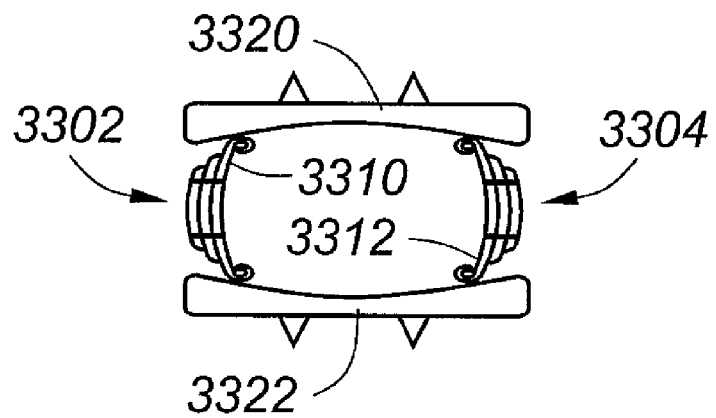
FIG. 33A is a coronal cross-section of another embodiment of the invention, wherein the spring component utilizes multiple leaf spring-like components.

FIG. 33A is a coronal cross section of another embodiment of the invention, wherein the spring component utilizes multiple leaf spring-like components 3302, 3304. In this configuration, the leaf spring-like components are preferably connected to hoops 3310, 3312 at the superior and inferior ends of the springs. Additional leaf spring-like components can be coupled to the outer surface of the inside leaf spring to increase the stiffness of the assembled spring component. Alternatively, circular hoops can be attached to the outside of the leaf springs to increase the spring's resistance to radial expansion. The ends of the leaf springs articulate may articulate with one or both ADR endplates 3320, 3322. FIG. 33A demonstrates articulation between the springs and both endplates. As discussed in FIG. 31, hydrogel-containing embodiments may place a membrane between the hydrogel and the spring to help hold the hydrogel within the spring.

Figure 33B:
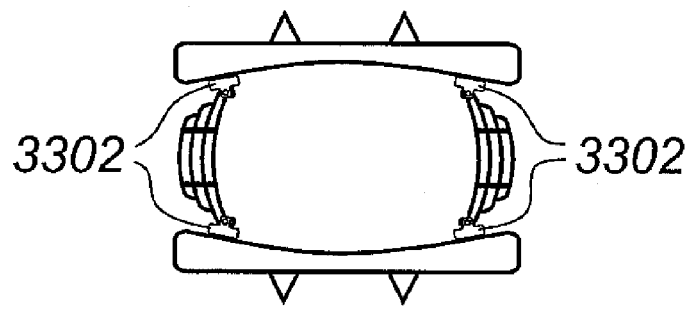
FIG. 33B is a coronal cross-section of another embodiment similar to that drawn in FIG. 33A, wherein the leaf springs articulate with one or more intermediate members.

FIG. 33B is a coronal cross section of another embodiment similar to that drawn in FIG. 33A, wherein the leaf springs articulate with intermediate member(s). The intermediate member(s) 3302 provide an improved articular surface for cooperation with the ADR endplates. FIG. 34A is a view of the side of the spring component drawn in FIG. 33A. Preferably, the leaf spring components overlap to decrease the gaps that occur between the components during compression of the spring component. The leaf spring represented by the cross hatched area of the drawing sits behind the two other leaf spring components. FIG. 34B is a view of the side of the spring component drawn in FIG. 34A during compression of the springs. The drawing illustrates the cooperation between adjacent leaf spring components to eliminate gaps between the components during compression of the springs.

FIG. 35A is a view of the top of the spring component drawn in FIG. 34A. FIG. 35B is a view of the top of the compressed spring component drawn in FIG. 34B. FIG. 36 is a cross section view of the hoops and leaf springs drawn in FIG. 34A.

FIG. 37A is a view of the side of another embodiment of the invention, including a mesh or basket-like weave spring component 3702 that cooperates with two ADR endplates 3704, 3706. The spring component preferably incorporates elastic and/or shape-memory materials. As with other embodiments, the spring component may also contain hoops that are capable of collapsing inside one another.

Figure 37C:
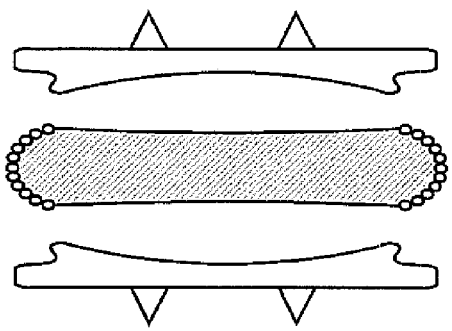
FIG. 37C is a coronal cross section of the ADR drawn in FIG. 37A during insertion.
Figure 37B:
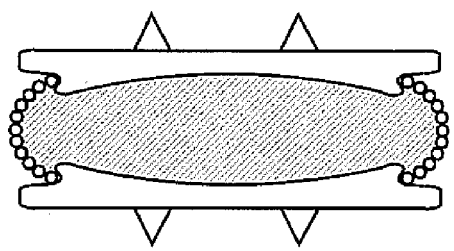
FIG. 37B is a coronal cross section of the ADR drawn in FIG. 37A.
Figure 37D:
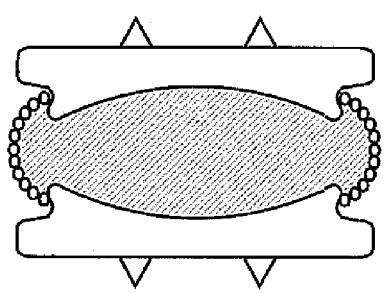
FIG. 37D is a coronal cross section of the ADR drawn in FIG. 37C following insertion.

FIG. 37B is a coronal cross section of the ADR drawn in FIG. 37A. The spring component surrounds a hydrogel, elastomer, or other compressible, resilient material. FIG. 37C is a coronal cross section of the ADR drawn in FIG. 37A during its insertion. The hoops on the top and bottom of the spring component have a first shape with a central opening larger than the projections from the ADR endplates. A hydrogel would be dehydrated. FIG. 37D is a coronal cross section of the ADR drawn in FIG. 37C after its insertion. The hoops on the top and bottom of the spring component contract around the projections from the ADR endplates, thus locking the components together. The hydrogel imbibes additional fluid after insertion of the ADR into the body.

Figure 38:
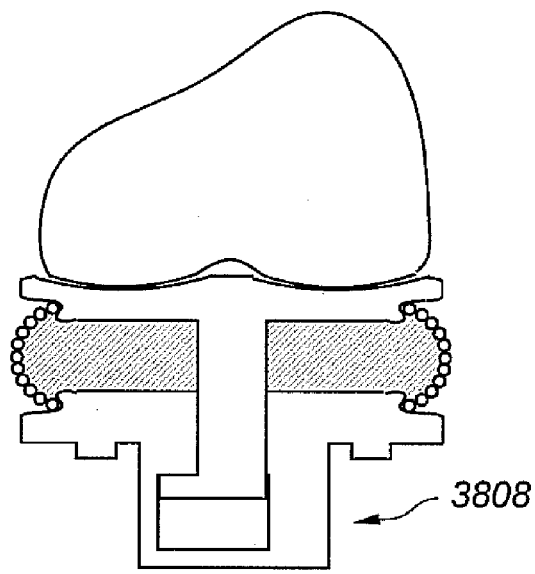
FIG. 38 is a coronal cross section of a Total Knee Replacement (TKR) embodiment of the invention.

FIG. 38 is a coronal cross section of the Total Knee Replacement (TKR) embodiment of the invention. A hydrogel-containing spring component, similar to that drawn in FIG. 37A, cushions the tibial component of the prosthetic knee. The articular component of the TKR pistons up and down a cylinder within the portion of the tibial component that attaches to the tibia. The articular portion of the tibia component preferably includes a reversible locking mechanism 3808 that prevents the articular component from dissociating from the component that is attached to the tibia. The articular and cushion components can be removed from the component that attaches to the tibia by rotating the piston to allow the enlargement at the end of the piston to fit through an enlarged opening in the cylinder.

Figure 39A:
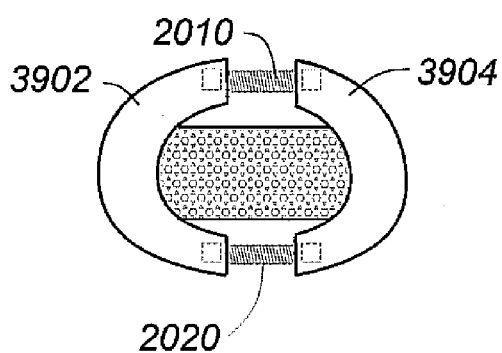
FIG. 39A is a view of the top of a spring component applicable to an ADR embodiment.

FIG. 39A is a top view of a different spring component used in an ADR embodiment according to the invention, wherein C-shaped metal articulating pieces 3902, 3904 are connected by two pieces of elastic material 3910, 3912. The dotted lines within the C-shaped pieces represent sockets in the C-shaped pieces and spheres at the ends of the elastic components. The dotted area of the drawing between the C-shaped components represents a polymeric or fiber dampening material. The assembled spring component is oval in shape to keep the open areas between the C-shaped pieces from rotating into a less desired position. For example, the ADR may be designed to keep the open areas between the C-shaped components in anterior and posterior positions to facilitate spinal flexion and extension.

Figure 39B:
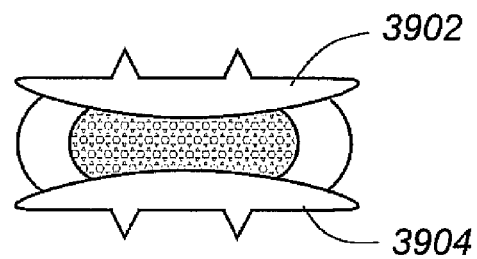
FIG. 39B is a coronal cross section through the ADR drawn in FIG. 39A.
Figure 39C:
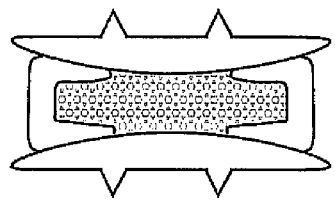
FIG. 39C is a coronal cross section of another embodiment of the ADR drawn in FIG. 39A.

FIG. 39B is a coronal cross section through the ADR drawn in FIG. 39A. Forces applied to the spine are transmitted to the spring component through two ADR endplates 3902, 3904. Force from the ADR EPs drive the C-ring articulating pieces apart, thus reducing the height of the ADR. The elastic tethers between the C-shaped pieces pull the C-shaped pieces together after the force is removed. The dampening material resists the C-shaped components return to their resting position, thus dampening the ADR. The dampening component is not bonded to either the ADR EPs or the C-shaped pieces. FIG. 39C is a coronal cross section of another embodiment of the ADR drawn in FIG. 39A. The C-shaped articulating pieces have concave inter surfaces to allow more room for the dampening component.

Figure 40:
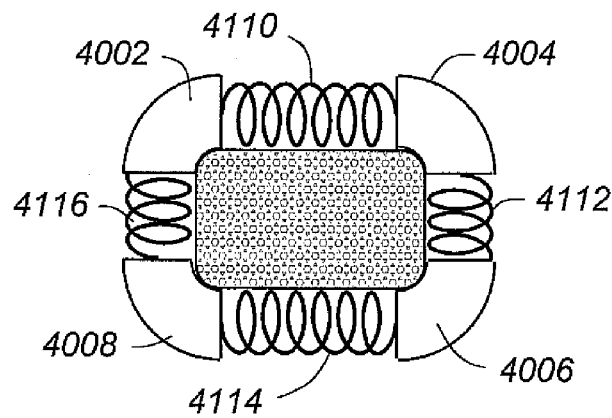
FIG. 40 is a top view of another ADR spring component embodiment.

FIG. 40 is a view of the top of another embodiment of a spring component according to the invention, wherein four articulating components 4002, 04, 06, 08 are connected by four springs 4110, 12, 14, 16. The openings between the articulating components allow room for more springs. The openings also facilitate flexion, extension, and lateral bending.

Figure 41A:
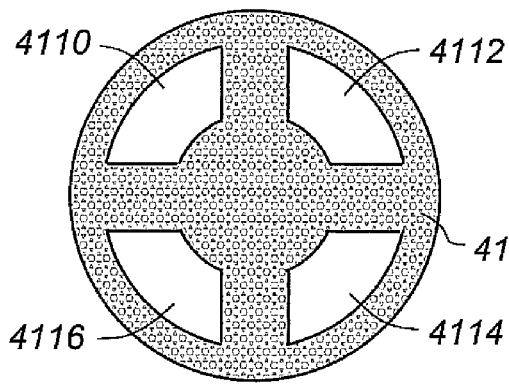
FIG. 41A is a top view of a further ADR spring component embodiment.
Figure 41B:
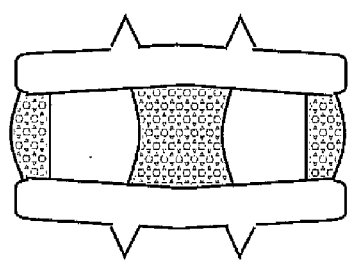
FIG. 41B is a coronal cross section of the embodiment of FIG. 41A.

FIG. 41A is a view of the top of another embodiment of the spring component according to the invention, wherein four articulating pieces are surrounded by an elastomer 4102. The articulating pieces fit into holes 4110, 12, 14, 16 in the elastomer. The articulating components, which may also have a circular shape when viewed from the top, fit into holes in the elastomer and are preferably not bonded to the elastomer. FIG. 41B is a coronal cross section of the embodiment of the device drawn in FIG. 41A.

Figure 42A:
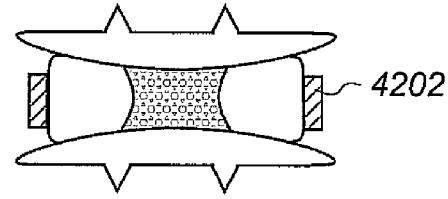
FIG. 42A is a coronal cross section of another embodiment of an ADR according to the invention.
Figure 42B:
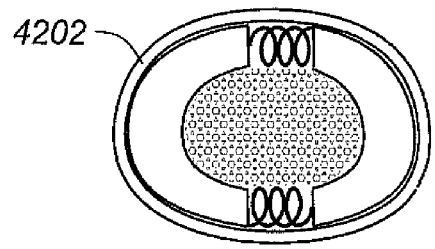
FIG. 42B is a top view of the spring component of FIG. 42A.

FIG. 42A is a coronal cross section of another embodiment of the ADR including articulating components surrounded by an elastomer ring 4202. Other materials with elastic or shape-memory properties, including Nitinol, may also be used for the ring. FIG. 42B is a view of the top of the embodiment of the spring component drawn in FIG. 42A. The elastomer ring assists the springs in returning the C-shaped articulating pieces to their resting position after the load is removed from the spine.

Figure 43A:
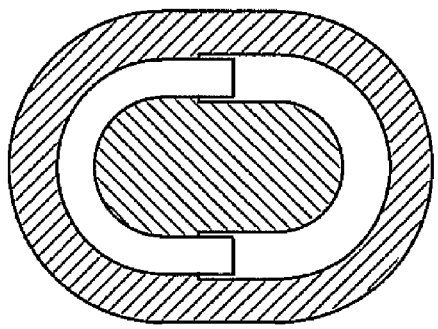
FIG. 43A is an axial cross section through another embodiment of a spring component, wherein the elastomer ring around the C-shaped articulating components supplies all the spring force.

FIG. 43A is an axial cross section through another embodiment of the spring component wherein the elastomer ring around the C-shaped articulating components supplies substantially all the spring force. Note that the springs between the C-shaped components have been eliminated. The C-shaped articulating components are drawn with an optional joint to prevent dissociation of the components. The ends of one articulating component piston in and out of the sockets in the ends of the second articulating component.

Figure 43B:
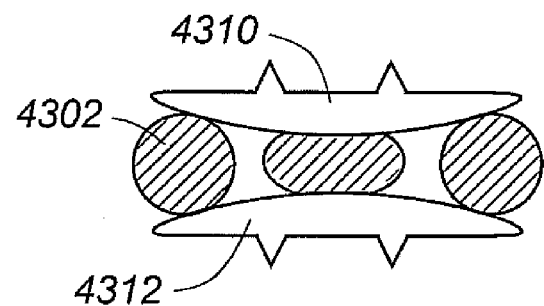
FIG. 43B is a coronal cross section through the embodiment of the invention of FIG. 43A.

FIG. 43B is a coronal cross section through the embodiment of the ADR drawn in FIG. 43A. Since the elastomer band 4302 does not touch the ADR EPs 4310, 4312, friction is reduced. The dampening component within the articulating components is not bond to either articulating component or the ADR EPs. The elastomer band is free from compression force from the ADR EPs. The dampening component between the articulating components is exposed to minimal compression from the ADR EPs. Compression by the ADR EPs drives articulating components apart. The elastomer ring limits how far apart the articulating components can separate, thus limiting compression of the dampening component. Compression of the dampening component can be eliminated by making the component too thin to touch the ADR EPs. An elastic metal with shape memory properties, such as Nitinol, could also be used as the band. The first shape of the band could include a large center opening that enables the spring component to be inserted after insertion of the ADR EPs. The band could assume a second shape with a smaller central opening, after insertion between the ADR EPs.

Figure 44:
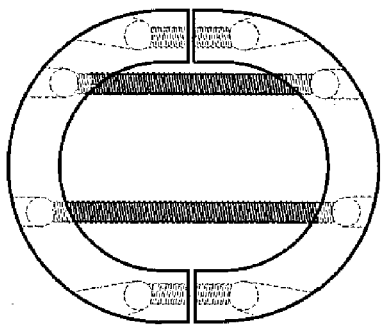
FIG. 44 is a top view of another embodiment of the spring component, wherein the articulating C-shaped components are opposing at rest.

FIG. 44 is a top view of the top of another embodiment of the spring component, wherein the articulating C-shaped components are opposing at rest. The spring components pull the articulating components together after loads are removed from the ADR. Impingement of the articulating components prevents the components from excessive recoil and repeated cycles of compression and recoil from a single quick application and removal of a load. Thus, the spring component in this embodiment does not require a dampening material. The dotted lines outline the course of the springs and the sphere shaped enlargements on the ends of the springs.

Figure 45A:
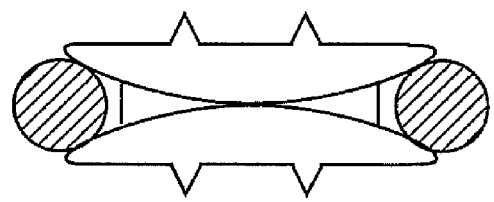
FIG. 45A is a coronal cross section of another embodiment of the invention.
Figure 45B:
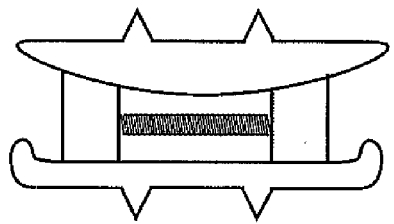
FIG. 45B is a coronal cross section of another embodiment of the ADR drawn in FIG. 45A.

FIG. 45A is a coronal cross section of another embodiment of the invention, wherein the endplates impinge at a predetermined amount of ADR compression, thereby limiting peak loads on the elastic band, bands, or cables. The concave exterior of the articulating components also protects the elastic band from friction against the ADR EPs. FIG. 45B is a coronal cross section of another embodiment of the ADR drawn in FIG. 45A. The articulating components impinge against stops on one or both of the ADR EPs at a predetermined amount of ADR Compression. As mentioned in the text of FIG. 45A, impingement of the ADR EPs limits peak loads on the elastic band, bands, or cables.

Figure 46A:
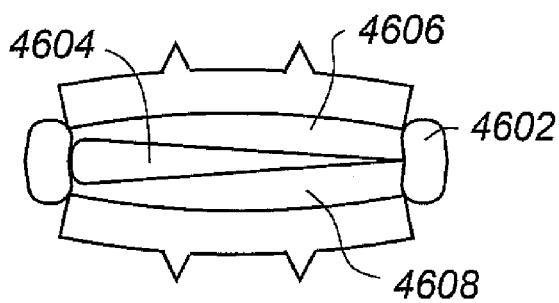
FIG. 46A is a coronal cross section of yet a different embodiment of the invention.
Figure 46B:
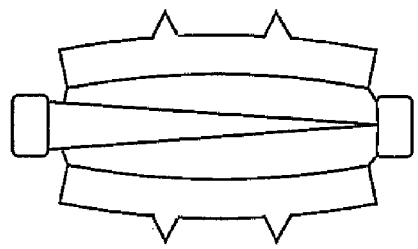
FIG. 46B is a coronal cross section of the embodiment of FIG. 46A with axial force applied to the ADR EPs.

FIG. 46A is a coronal cross section of another embodiment of the invention, wherein a material 4602 with elastic properties surrounds three articulating components. A center, preferably wedge-shaped articulating component 4604 fits into a wedge-shaped opening between the two components 4606, 4608 that articulate with the ADR EPs. FIG. 46B is a coronal cross section of the embodiment of the ADR drawn in FIG. 46A with axial force applied to the ADR EPs. The wedge shaped articulating component is forced from between the two articulating components that articulate with the ADR EPs. The elastomeric hoop forces the wedge shaped component into its resting position, when the load is removed from the ADR EPs.

Figure 47A:
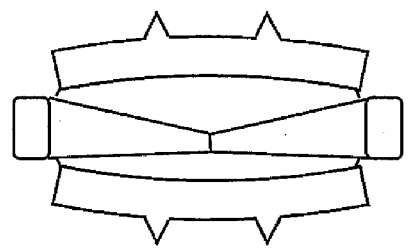
FIG. 47A is a coronal cross section of another embodiment of the ADR, including two wedge-shaped components.
Figure 47C:
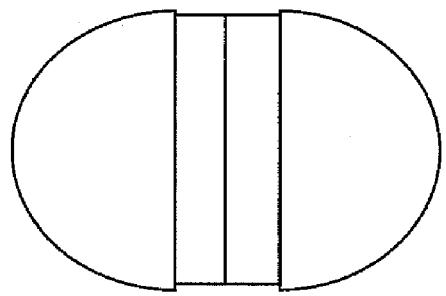
FIG. 47C is a view of the bottom of the wedge-shaped components and one of the components that articulates with the ADR EPs from the embodiment of FIG. 47B.
Figure 47B:
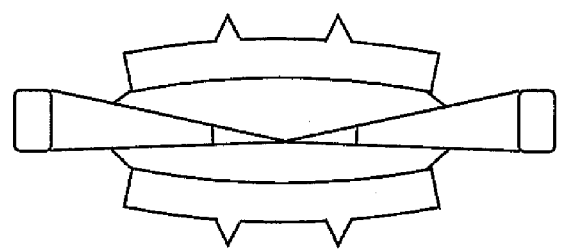
FIG. 47B is a coronal cross section of the embodiment of FIG. 47A with axial force applied to the ADR EPs.

FIG. 47A is a coronal cross section of another embodiment of the ADR, including a plurality of wedge-shaped components. FIG. 47B is a coronal cross section of the embodiment of the ADR drawn in FIG. 47A with axial force applied to the ADR EPs. FIG. 47C is a view of the bottom of the wedge shaped components and one of the components that articulates with the ADR EPs from the embodiment of the ADR drawn in FIG. 47B.

Figure 47D:
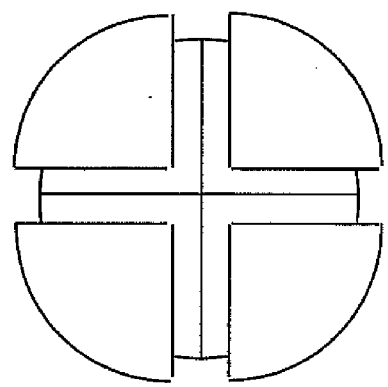
FIG. 47D is a view of the bottom of four wedge-shaped components and an alternative embodiment of the component that articulates with the ADR EPs.

FIG. 47D is a view of the bottom of four wedge-shaped components and an alternative embodiment of the component that articulates with the ADR EPs. Similar to the embodiment of the ADR drawn in FIG. 47C, the component that articulates with the ADR EP, forces the wedge-shaped components apart as axial loads are applied to the ADR EPs. The separation between the one pair of wedge shaped components may be larger than the separation between the second pair of wedge shaped components during spinal motion in one direction. For example, spinal flexion forces the anterior pair of wedges apart. Spinal flexion also forces the anterior pair of wedges from the posterior pair of wedges. Spinal flexion does not force the posterior pair of wedges apart.

Figure 48:
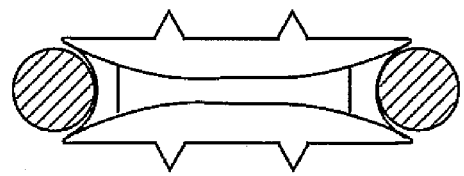
FIG. 48 is a coronal cross section of another embodiment of the ADR, wherein the articulating surfaces of the ADR EPs have a varying radii of curvature.

FIG. 48 is a coronal cross section of another embodiment of the ADR, wherein the articulating surfaces of the ADR EPs have a varying radii of curvature. In particular, the radius at the periphery of the ADR EPs is smaller than the radius in the central portion of the ADR EPs. The smaller radius in the periphery of the ADR EPs increases the rate of ADR height change to ADR diameter change ratio. The larger radius in the central portion of the ADR EPs increases the surface contact when the plates impinge at maximum loads. The central portion of the ADR EPs could also be another shape, including flat.

Figure 49A:
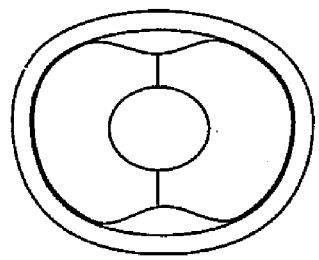
FIG. 49A is the view of the top of an alternative embodiment of the C-shaped components and the elastic hoop.
Figure 49B:
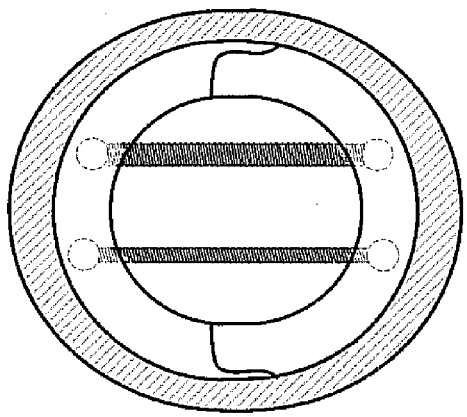
FIG. 49B is a view of the top of an alternative embodiment of the C-shaped components and the elastic hoop.

FIG. 49A is the view of the top of an alternative configuration wherein the C-shaped components have concavities to help prevent pinching the elastic hoop. FIG. 49B is a view of the top of an alternative embodiment of the C-shaped components and the elastic hoop. The C-shaped components overlap to help prevent pinching the elastic hoop. The elastic cords that connect the C-shaped pieces preferably have different durometers to accommodate spinal motion in different directions. For example, the elastic cords and/or the elastic hoop could facilitate spinal flexion relative to spinal extension.

Figure 49C:
FIG. 49C is a view of the sides of a portion of the C-shaped pieces drawn in FIG. 49B.
Figure 49D:
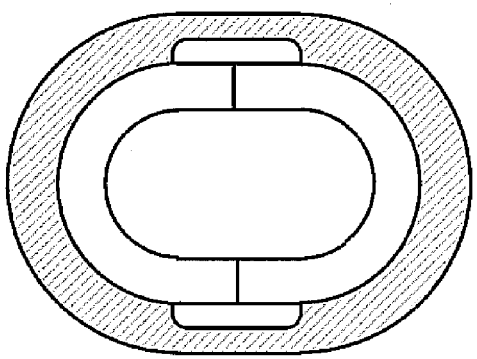
FIG. 49D is the view of the top of an alternative embodiment of the C-shaped components and the elastic hoops.
Figure 49E:
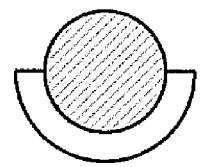
FIG. 49E is a cross section of a C-shaped piece and the sleeve drawn in FIG. 49D.

FIG. 49C is a view of the sides of a portion of the C-shaped pieces drawn in FIG. 49B. FIG. 49D is the view of the top of an alternative embodiment of the C-shaped components and the elastic hoops. The assembled C-shape components form an oval shape that helps prevent rotation of the C-shaped components. A flexible sleeve lies between the C-shaped pieces and the elastic hoop to prevent pinching the elastic hoop. Alternatively, the flexible sleeve could be placed over the C-shaped pieces. FIG. 49E is a cross section of a C-shaped piece and the sleeve drawn in FIG. 49D. The flexible sleeve could also fully surround the C-shaped pieces or the hoop at the junction of the C-shaped pieces.

Figure 50A:
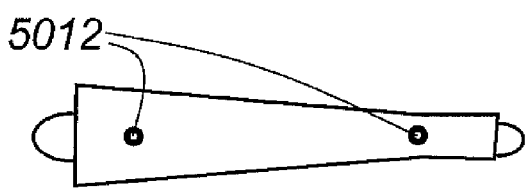
FIG. 50A is a sagittal cross section of another embodiment of the C-shaped pieces and the elastic hoop.
Figure 50B:
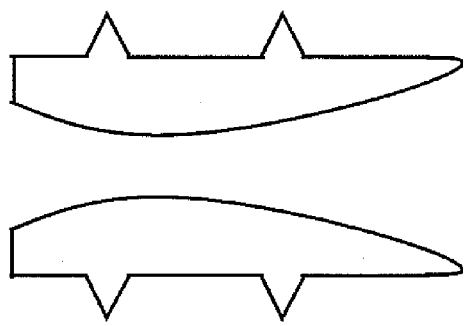
FIG. 50B is a sagittal cross section of the ADR EPs in another embodiment of the ADR.

FIG. 50A is a sagittal cross section of another embodiment of the C-shaped pieces and an elastic hoop. The C-shaped pieces are trapezoidal shaped to fit normal disc anatomy. The circles 5012 represent the enlarged ends of the elastic cords that connect the C-shaped pieces. FIG. 50B is a sagittal cross section of the ADR EPs in another embodiment of the ADR. The ADR EPs are trapezoidal to fit the normal disc anatomy.

Figure 51A:
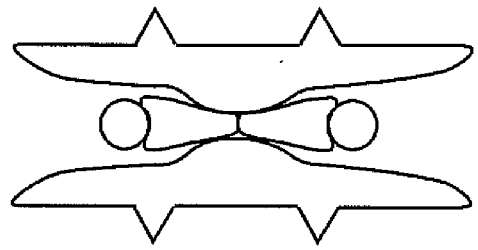
FIG. 51A is a coronal cross section of another embodiment of the device.
Figure 51B:
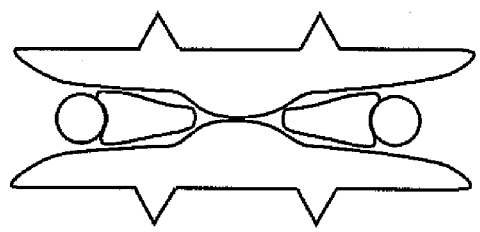
FIG. 51B is a coronal cross section of the embodiment of the ADR drawn in FIG. 51A with a load being applied.

FIG. 51A is a coronal cross section of another embodiment wherein the articulating surfaces of the ADR EPs are flat at their periphery to accommodate the articulating pieces and the elastic hoop. The articulating pieces are in contact along the entire junction between the components. FIG. 51B is a coronal cross section of the embodiment of the ADR drawn in FIG. 51A with load applied to the ADR.

Figure 52A:
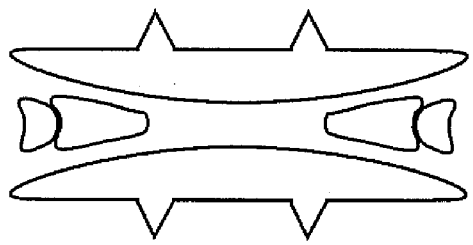
FIG. 52A is a coronal cross section of another embodiment of an ADR according to the invention.

FIG. 52A is a coronal cross section of another embodiment of the invention, wherein the elastic hoop is made of a shape-memory material such as Nitinol. The first shape of the material eases insertion of the C-shaped pieces and the elastic hoop after ADR EP insertion. The first shape of the hoop could be thinner and/or larger in diameter than the second shape of the hoop. Alternatively, the first state of the material may be more malleable than the second state of the material. The hoop could also be a composite of materials such as, Nitinol and an elastomer.

Figure 52B:
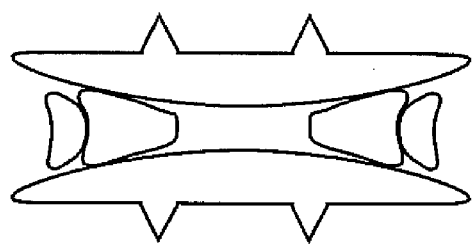
FIG. 52B is a coronal cross section of the embodiment of FIG. 52A with the elastic hoop in its second shape.
Figure 53:
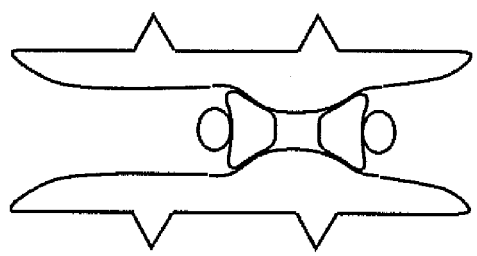
FIG. 53 is a sagittal cross section of yet a further, different embodiment of an ADR according to the invention.

FIG. 52B is a coronal cross section of the embodiment of the ADR drawn in FIG. 52A with the elastic hoop in its second shape. FIG. 53 is a sagittal cross section of another embodiment of the ADR. The convexities on the ADR EPs are preferably located in the posterior half of the ADR.

Figure 54A:
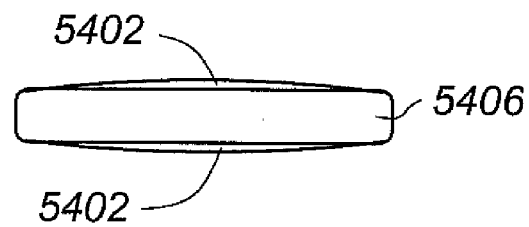
FIG. 54A is a side view of an embodiment of the invention designed for placement in a disc space without ADR endplates.
Figure 54B:
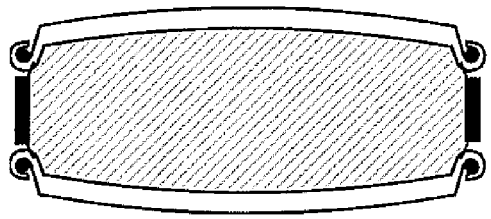
FIG. 54B is a coronal cross section of the ADR of FIG. 54A.
Figure 54C:
FIG. 54C is a coronal cross section of another version of the ADR of FIG. 54B.

FIG. 54A is a side view of another embodiment designed for placement in the disc space without ADR endplates. An elastomer with bias ply fabric (5402), is attached to an elastic hoop 5406. FIG. 54B is a coronal cross section of the ADR draw in FIG. 54A. The black area of the drawing represents the elastic hoop made of a material such as Nitinol. In the preferred embodiment of the drawing the ADR is filled with a hydrogel. FIG. 54C is a coronal cross section of another embodiment of the ADR drawn in FIG. 54B. The elastic hoop surrounds a portion of the superior and inferior surfaces of the hydrogel.

Figure 55A:
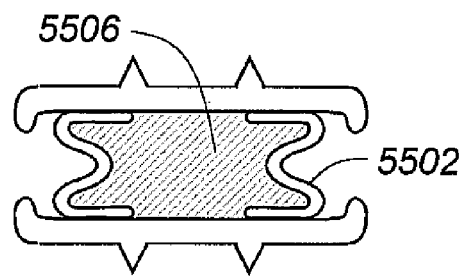
FIG. 55A is a coronal cross section of another alternative embodiment of the invention.
Figure 55B:
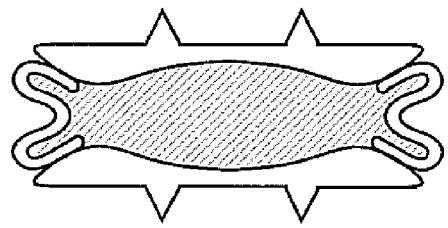
FIG. 55B is a coronal cross section of a different version of the ADR of FIG. 55A.

FIG. 55A is a coronal cross section of another embodiment of an ADR including an elastic hoop 5502 that surrounds a portion of a hydrogel component 5506. The elastic hoop articulates with the ADR endplates. The ADR endplates have raised lips to help prevent the extrusion of the cushioning component. FIG. 55B is a coronal cross section of another embodiment of the ADR drawn in FIG. 55A. The ADR endplates are shaped to prevent the extrusion of the cushioning component. The shape of the ADR endplate also assists the hydrogel component in expanding the elastic hoop as axial pressure is applied to the ADR.

Figure 56A:
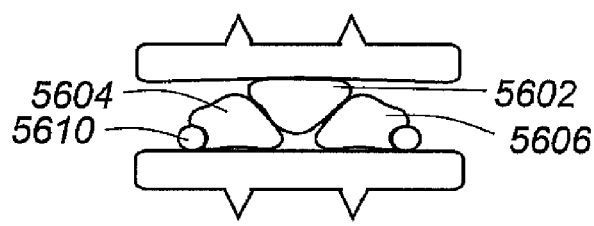
FIG. 56A is a coronal cross section of through another embodiment of the invention.
Figure 56B:
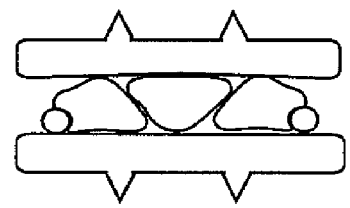
FIG. 56B is a coronal cross section of the ADR of FIG. 56A with an axial load applied.
Figure 56C:
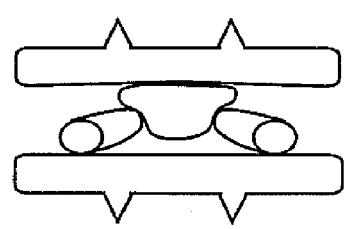
FIG. 56C is an alternative version of the ADR of FIG. 56B.

FIG. 56A is a coronal cross section of through another ADR embodiment including three or more articulating components 5602, 04, 06 made of a material with good surface wear characteristics held together by an elastic component 5610. FIG. 56B is a coronal cross section of the ADR drawn in FIG. 56A with axial load applied to the ADR. The superior articulating component wedges the inferior articulating components open. The elastic component forces the articulating components into their resting position as the force is removed from the ADR. In the preferred embodiment, the articulating components impinge on both of the ADR endplates at a predetermined load. Impingement of the articulating pieces, with the ADR endplates, protects the elastic component from excessive force. Furthermore, the impingement protects the facet joints from excessive force. FIG. 56C is an alternative embodiment including ball-and-socket joints between the articulating components that facilitate motion between the components.

Figure 57A:
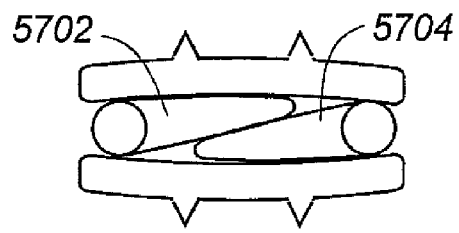
FIG. 57A is a coronal cross section of yet a different alternative embodiment of the invention.
Figure 57B:
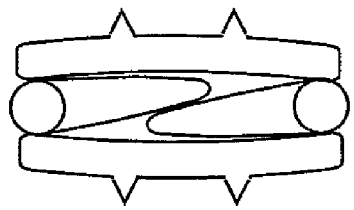
FIG. 57B is a coronal cross section of the embodiment of FIG. 57A with an axial load applied.

FIG. 57A is a coronal cross section of yet a different ADR embodiment wherein two articulating components 5702, 04 cooperate on an inclined plane. Axial loads on the ADR cause the articulating components to slide along the inclined plane. In an alternative embodiment, the inclined plane courses from anterior to posterior. An elastic hoop or C-shaped component forces the articulating components together. The articulating components could be tethered together by a projection from one component that slides in a slot in the second component. FIG. 57B is a coronal cross section of the embodiment of the ADR with an axial load applied to the ADR.

Figure 58A:
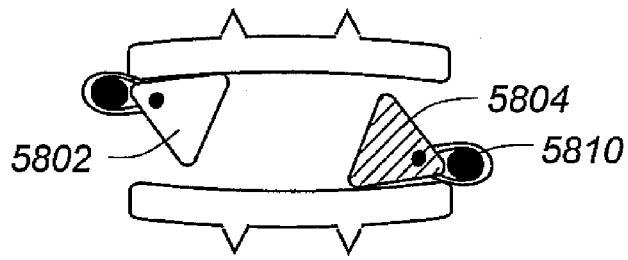
FIG. 58A is a coronal cross section of yet a further alternative embodiment of the invention.
Figure 58B:
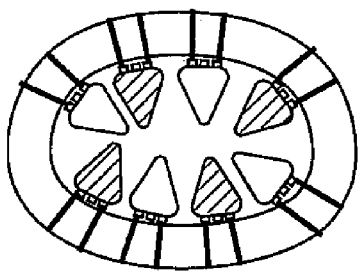
FIG. 58B is a view of the top of the cushioning component drawn in FIG. 58A.
Figure 58C:
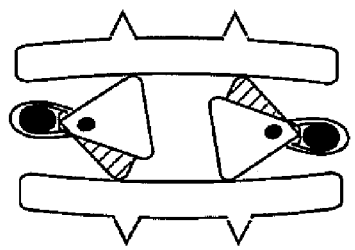
FIG. 58C is a coronal cross section of the ADR of FIG. 58A.
Figure 58D:
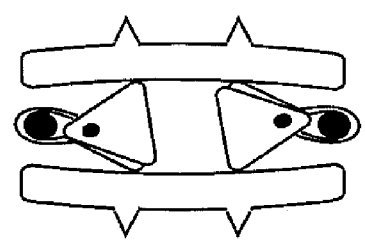
FIG. 58D is a coronal cross section of the ADR of FIG. 58C with axial load applied.
Figure 58E:
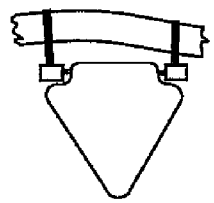
FIG. 58E is a view of the top of one of the hinged articulating components drawn in FIG. 58B.
Figure 58F:
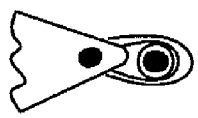
FIG. 58F is an enlarged coronal cross section of one of the articulating hinged components drawn in FIG. 58A.

FIG. 58A is a coronal cross section of an alternative ADR embodiment wherein hinged articulating components 5802, 04 cooperate with an elastic hoop or C-shaped component 5810. The hinged articulating components are preferably loosely attached to the elastic hoop. FIG. 58B is a view of the top of the cushioning component drawn in FIG. 58A. FIG. 58C is a coronal cross section of the ADR drawn in FIG. 58A. FIG. 58D is a coronal cross section of the ADR drawn in FIG. 58C with axial load applied to the ADR. FIG. 58E is a view of the top of one of the hinged articulating components drawn in FIG. 58B. FIG. 58F is an enlarged coronal cross section of one of the hinged articulating components drawn in FIG. 58A.

Figure 59:
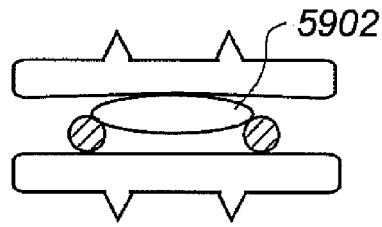
FIG. 59 is a coronal cross section of a different further alternative embodiment of the invention.

FIG. 59 is a coronal cross section of an alternative embodiment of the ADR wherein an articulating component 5902 articulates between an elastic hoop or C-shaped component and the ADR endplates. Axial compression forces the articulating component to wedge open the elastic hoop or C-shaped component. Note that the elastic hoop or C-shaped component is not congruent with the inferior ADR endplate. The top of the articulating component need not be congruent with the top ADR endplate. Non-congruent surfaces between the ADR endplates and the articulating components facilitate ADR insertion. Non-congruent surfaces do not require an exact fit for proper articulation.

Figure 60:
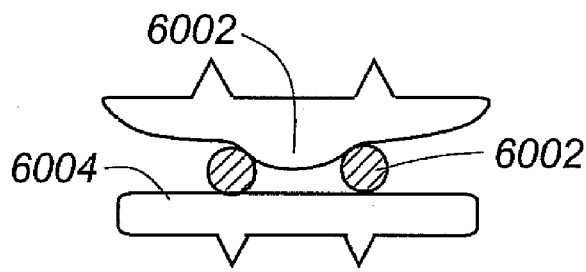
FIG. 60 is a coronal cross section of another ADR embodiment with non-congruent articulating surfaces.

FIG. 60 is a coronal cross section of another embodiment of the ADR with non-congruent articulating surfaces. A ball-shaped projection 6002 from one ADR endplate cooperates with an elastic hoop or C-shaped component 6004 and a second ADR endplate 6006.

Figure 61A:
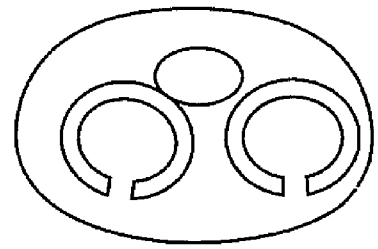
FIG. 61A is an axial cross section through another embodiment of an ADR according to the invention.
Figure 61B:
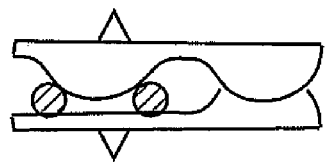
FIG. 61B is a sagittal cross section through the ADR of FIG. 61A.

FIG. 61A is an axial cross section through another embodiment, wherein one or more ball-shaped projections from one ADR Endplate (EP) articulate(s) with a second ADR EP. The second ADR EP may have a socket to receive the ball-shaped component. Elastic hoops or C-shaped rings are used to cushion the ADR. FIG. 61B is a sagittal cross section through the ADR drawn in FIG. 61A. Ball-shaped projections from one ADR EP cooperate with elastic hoops or C-shaped components to cushion the ADR. Articulation through the ball and socket joint in the posterior aspect of the ADR prevents transferring loads to the facet joints during axial compression of the ADR.

Figure 61C:
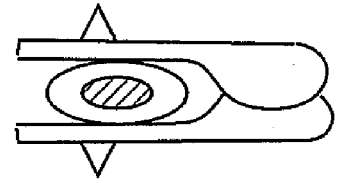
FIG. 61C is a sagittal cross section through the ADR of FIG. 61B showing one of many alternative cushioning components.
Figure 61D:
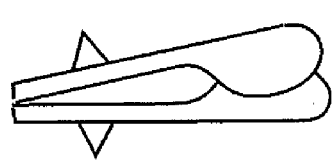
FIG. 61D is a sagittal cross section of the ADR endplates (EPs) of FIG. 61C.

FIG. 61C is a sagittal cross section through the ADR drawn in FIG. 61B with one of many alternative cushioning components. For example, a combination titanium or other metal and elastomer component may be used as a cushioning component. Shape-memory technology is preferably used to attach a removable stop to the front of the ADR. For example, the stop could be made of Nitinol. The hole in the stop could contract around a projection fro the ADR EP. The stop serves to prevent extrusion of the modular cushioning component. The stop may also impinge on the upper ADR EP during maximum loads on the ADR. Impingement of the stop on the ADR EP protects the cushion component from excessive loads. FIG. 61D is a sagittal cross section of the ADR EPs drawn in FIG. 61C. Rotation through the ball-and-socket joint facilitates insertion of the ADR.

Figure 62:
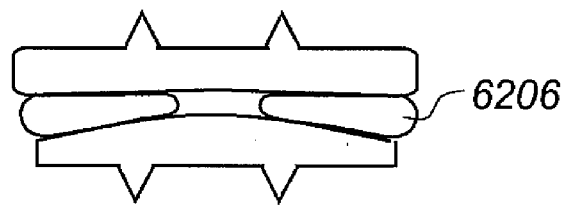
FIG. 62 is a sagittal cross section through another ADR embodiment.

FIG. 62 is a sagittal cross section through another embodiment wherein a hoop or C-shaped component 6202 articulates between two ADR EPs. The hoop or C-shaped component can be made of an elastic material. One of the ADR EPs can be a cemented polyethylene component. The flat articulating surface of the ADR EP and the flat upper surface of the hoop or C-shaped articulating component facilitate insertion of the ADR. Note that the two ADR EPs do not require precise placement to permit articulation between the components.

Figure 63A:
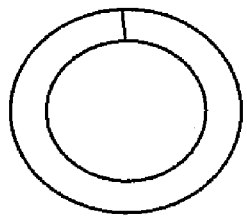
FIG. 63A is a view of the top of a C-shaped elastic component in a closed position.
Figure 63B:
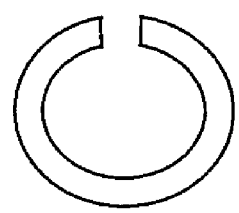
FIG. 63B is a view of the top of the C-shaped elastic component draw in an open position.

FIG. 63A is a view of the top of a C-shaped elastic component in a closed position. FIG. 63B is a view of the top of the C-shaped elastic component draw in an open position. The ends of the C-shaped component collide when they close to prevent recoil past a neutral, closed position. The design of the C-shaped component prevents excessive recoil and bouncing of the ADR.

Figure 64A:
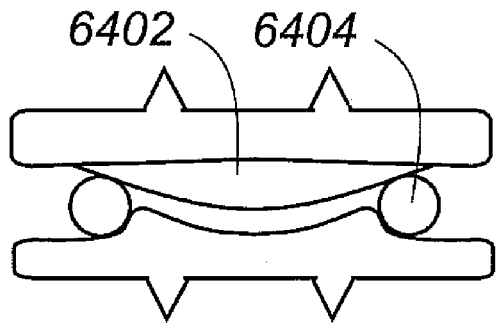
FIG. 64A is a coronal cross section through another embodiment of the ADR.
Figure 64B:
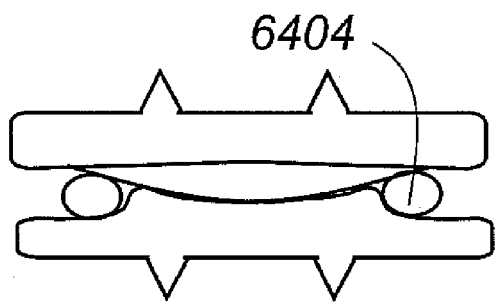
FIG. 64B is a coronal cross section of the ADR drawn in FIG. 64A with axial load applied.
Figure 64C:
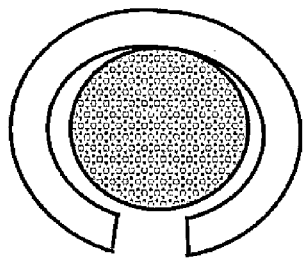
FIG. 64C is a view of the top of the elastic C-shaped component with shape memory, and an associated articulating component.
Figure 64D:
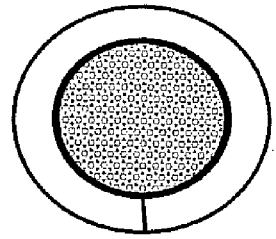
FIG. 64D is a view of the top of the C-shaped component and the articulating component, after the C-shaped component has assumed a final shape.

FIG. 64A is a coronal cross section through another ADR embodiment wherein a mobile spacer component 6402 articulates between the ADR EPs and an elastic hoop or C-shaped member 6404. The flat surface between the articulating spacer and one of the ADR EPs allows the spacer to "self center" over the shape in the second ADR EP. FIG. 64B is a coronal cross section of the ADR drawn in FIG. 64A with axial load applied to the ADR. The drawing also illustrates how the articulating component can slide along the flat surface of the ADR EP, thus aligning the articulating component over the concavity in the second ADR EP. FIG. 64C is a view of the top of the elastic C-shaped component, preferably constructed with a shape-memory material, and the articulating component. The first shape of the C-shaped component facilitates insertion of the C-shaped component, and the articulating component, after insertion of the ADR EPs. FIG. 64D is a view of the top of the C-shaped component and the articulating component, after the C-shaped component has assumed a final shape.

Figure 65A:
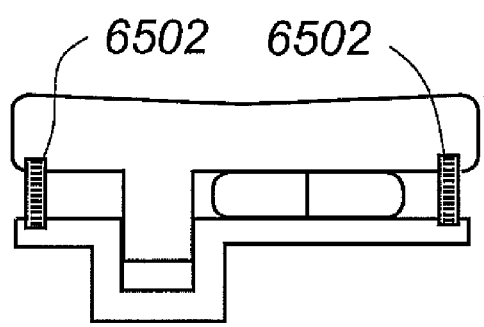
FIG. 65A is a sagittal cross section of an alternative sealing mechanism.

FIG. 65A is a sagittal cross section of an elastomerics membrane 6502 used to seal a cushioned TKR according to the invention. The membrane prevents debris from migrating out of the device. The membrane can also hold a lubricating fluid, such as vegetable oil, within the TKR. Spherical projection from the articulating component and or the second metal component, wedge open an elastic hoop component.

Figure 65B:
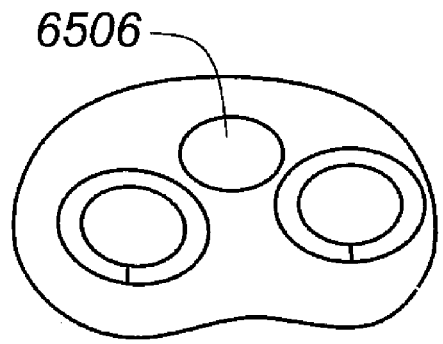
FIG. 65B is an axial cross section of the embodiment of FIG. 65A.

FIG. 65B is an axial cross section of the embodiment of the device drawn in FIG. 65A. The piston of the articulating component is represented by 6506. The embodiment of the device drawn in FIG. 65B uses two C-shaped elastic hoops. Alternatively, one or more wave washers, such as, ring shaped or spiral shaped wave washers could cushion the TKR or Total Hip Replacement (THR). One or more Belleville washers could also cushion the TKR or THR. For example, Belleville washers such as spirally slotted Belleville washers with or without radially extending grooves, Belleville washers with radially spaced concentric grooves, and radially thinning Belleville washers could be used.

Figure 66:
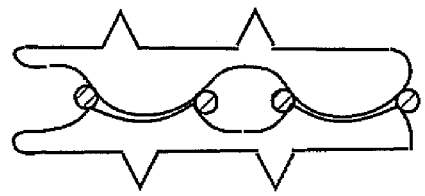
FIG. 66 is an alternative, cushioned ADR embodiment.

FIG. 66 is an alternative, cushioned, embodiment of an ADR wherein spherical projections from the upper ADR EP wedge open elastic hoops or elastic C-shaped components in response to axial loads on the ADR. The inferior ADR EP may have concavities to receive the spherical projections from the superior ADR EP.

Figure 67A:
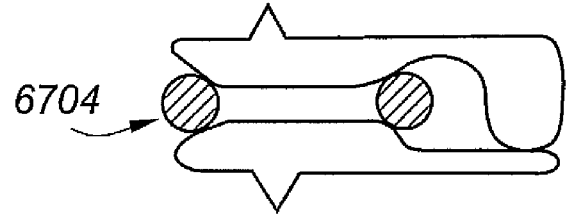
FIG. 67A is a sagittal cross section of an alternative embodiment of the ADR of FIG. 66.

FIG. 67A is a sagittal cross section of an alternative configuration of the ADR of FIG. 66, wherein a spherical projection from one ADR EP articulates with the flat portion of a second ADR EP. The articulation between the spherical projection and the flat portion of the ADR EP allows translation of one ADR EP relative to the other ADR EP. The articulation also requires less precise placement of the ADR EPs. The anterior portion of the ADR is cushioned by one or two elastic hoops or elastic C-shaped components 6704. The C-shaped components can be an elongated C or oval. In the preferred embodiment, the opening of the C-shaped component lies in the anterior portion of the ADR to facilitate spinal flexion. An oval shape helps prevent rotation of the opening away from an anterior location.

Figure 67B:
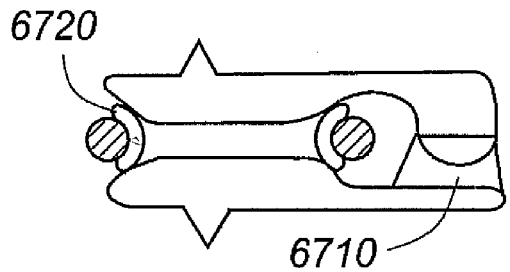
FIG. 67B is a sagittal cross section of an alternative configuration of the ADR of FIG. 67A.

FIG. 67B is a sagittal cross section of an alternative configuration of the ADR drawn in FIG. 67A. The spherical projection from the superior ADR EP in this case articulates with washer 6710 with a concavity on the superior surface of the washer. The flat inferior surface of the washer articulates with the inferior ADR EP. The washer can be snapped or otherwise loosely connected to the spherical projection from the upper ADR EP. The washer may be slightly non-congruent with the spherical projection. The elastic hoop or C-shaped component lies outside of two or more C-shaped components of a harder material 6720 such as chrome cobalt.

Figure 68:
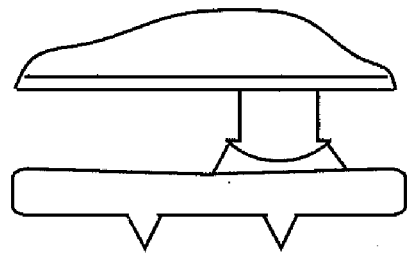

FIG. 68 is a sagittal cross section through another embodiment of the ADR. The spherical projection from the superior ADR EP travels in a slot in the superior ADR. In the preferred embodiment of the ADR, the slot is located in the midline of the ADR EP as measured from left to right and in the posterior half of the ADR as measured from front to back. The spherical projection could also be fixed to the superior ADR EP at a certain point along the slot. For example a shape memory fastener could connect the spherical projection to the ADR EP.

Figure 69A:
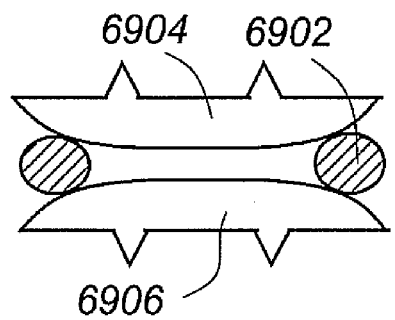

FIG. 69A is a sagittal cross section of another embodiment of the ADR wherein an elastic hoop or C-shaped component 6902 articulates with convex portions of the ADR EPs 6904, 06. The flat surfaces at the center of the ADR EPs allow the ADR EPs to come closer together before impinging on one another. The articulating elastic component preferably features a spherical cross section to cooperate with spherical surfaces of the ADR EPs. The preferred shapes maintain good surface apposition during rotation of the ADR EPs and expansion of the elastic component.

Figure 69B:
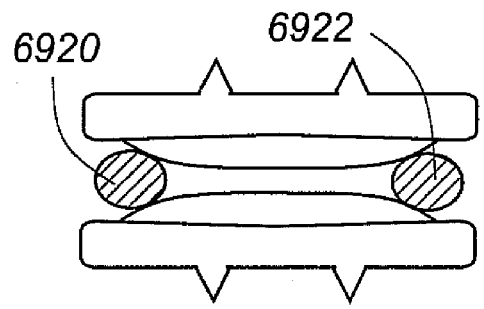

FIG. 69B is a sagittal cross section of another embodiment of the ADR drawn in FIG. 69A. Spacers 6920, 22 articulate between the ADR EPs and the elastic hoop or C-shaped component. The spacers and the elastic hoop can be placed after ADR EP insertion. A retaining mechanism is used to hold the spacers and hoop in position. For example, using shape memory technology, a projection from the inferior ADR EP can change shape in the hole of a retaining piece, thus locking the two components together.

Figure 70A:
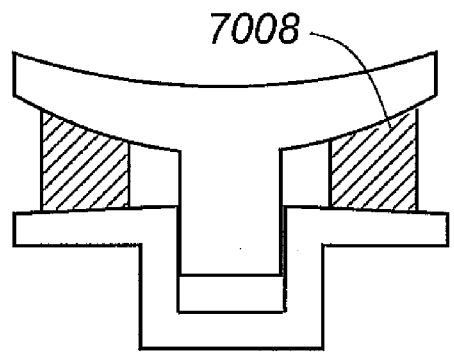

FIG. 70A is a sagittal cross section of another TKR embodiment including a superior component that articulates with a femoral component of a TKR. Both articulating components could be made of a hard material such as zirconium oxide ceramic or aluminum oxide ceramic. A wedge-shaped central component 7008 cooperates along inclined planes of the superior and inferior components. The wedge shaped central component could be made of a wear-resistant material such as polyethylene. The inferior surface of the inferior component could be treated to promote bone growth.

Figure 70B:
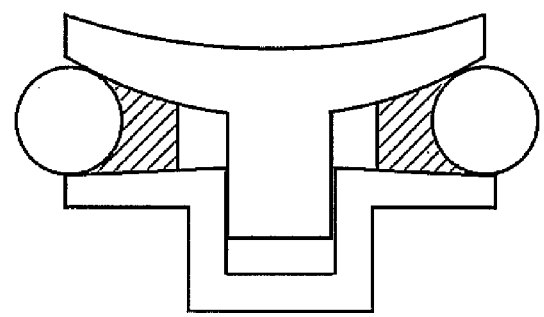

FIG. 70B is a sagittal cross section of another embodiment of the device drawn in FIG. 70A. Two or more central wedge shaped components cooperate along inclined planes with the superior and inferior components. An elastic hoop or C-shaped component resists expansion of the central wedge shaped components. The wedge shaped components could be made of ceramic, chrome cobalt, or other material with good wear characteristics.

Figure 70C:
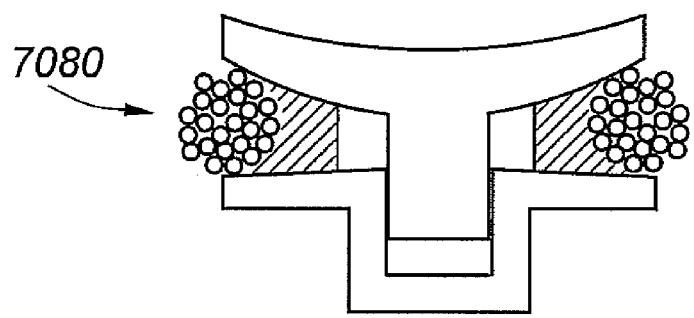
Figure 70D:
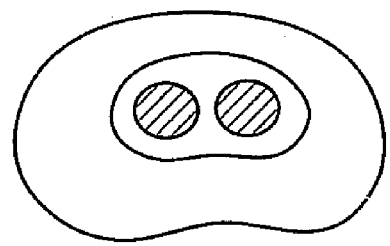

FIG. 70C is a sagittal cross section of another embodiment of the device drawn in FIG. 70B, showing how multiple elastic hoops 7080 resist the expansion of the wedge shaped central components. FIG. 70D is an axial cross section of the embodiment of the TKR drawn in FIG. 70A. Two pistons are preferred in this device to prevent surface shear on the polyethylene component, and for rotation of the superior articulating component. Alternatively, a single piston that has a non-circular cross section, could also be used to prevent rotation. A single piston with a circular cross section could also be used.

I claim:

1. An artificial disc replacement (ADR), comprising:

a C-shaped shape-memory spring component having two ends and a height defining an interior volume; and a generally biconvex component adapted for articulation between an endplate of a vertebral body and the C-shaped spring component, the biconvex component including a portion that extends outwardly beyond the height of the spring component, such that pressure on the biconvex component forces the biconvex component into the interior volume of the spring component, causing the ends of the C-shaped component move apart during axial loads on the spine and during spinal flexion, but wherein the shape memory returns the C-shaped component and biconvex components to their neutral positions as the axial load is removed or the spine is returned to a neutral position.

2. The ADR of claim 1, wherein one or both of the components are coupled to the vertebral bodies through endplate resurfacing components.

* * * * *